(12) United States Patent
Adalsteinsson et al.

(10) Patent No.: US 10,776,608 B2
(45) Date of Patent: Sep. 15, 2020

(54) SYSTEMS, METHODS, AND APPARATUS FOR IN VITRO SINGLE-CELL IDENTIFICATION AND RECOVERY

(71) Applicant: Massachusetts Institute of Technology, Cambridge, MA (US)

(72) Inventors: Viktor A. Adalsteinsson, Wakefield, MA (US); Denis Loginov, Dorchester Center, MA (US); J. Christopher Love, Somerville, MA (US); Alan Stockdale, Providence, RI (US); Todd Gierahn, Brookline, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 107 days.

(21) Appl. No.: 16/102,118

(22) Filed: Aug. 13, 2018

(65) Prior Publication Data
US 2019/0005304 A1    Jan. 3, 2019

Related U.S. Application Data

(62) Division of application No. 14/997,439, filed on Jan. 15, 2016, now Pat. No. 10,078,778.
(Continued)

(51) Int. Cl.
*G06K 9/00* (2006.01)
*B01L 3/00* (2006.01)
(Continued)

(52) U.S. Cl.
CPC ........ *G06K 9/00147* (2013.01); *B01L 3/5085* (2013.01); *G01N 15/1425* (2013.01);
(Continued)

(58) Field of Classification Search
CPC ..... B01L 2300/0654; B01L 2300/0829; B01L 2300/0851; B01L 2300/0896;
(Continued)

(56) References Cited

U.S. PATENT DOCUMENTS 4,175,860 A    11/1979 Bacus
4,207,554 A    6/1980 Resnick et al.
(Continued)

FOREIGN PATENT DOCUMENTS

EP    2 170 514 B1    5/2013
WO    WO-2009/063462 A2    5/2009

OTHER PUBLICATIONS

International Search Report, PCT/US2016/013724 (Systems, Methods, and Apparatus for in Vitro Single-Cell Identification and Recovery, filed Jan. 15, 2016), issued by ISA/European Patent Office, 6 pages, dated Jul. 19, 2016.
(Continued)

*Primary Examiner* — Francis Geroleo
(74) *Attorney, Agent, or Firm* — Choate, Hall & Stewart LLP; William R. Haulbrook; Alexander D. Augst

(57) ABSTRACT

Described herein are systems, methods, and apparatus for automatically identifying and recovering individual cells of interest from a sample of biological matter, e.g., a biological fluid. Also described are methods of enriching a cell type of interest. These systems, methods, and apparatus allow for coordinated performance of two or more of the following, e.g., all with the same device, thereby enabling high throughput: cell enrichment, cell identification, and individual cell recovery for further analysis (e.g., sequencing) of individual recovered cells.

16 Claims, 16 Drawing Sheets

Related U.S. Application Data

(60) Provisional application No. 62/104,036, filed on Jan. 15, 2015.

(51) Int. Cl.
| | |
|---|---|
| *G01N 15/14* | (2006.01) |
| *G01N 35/00* | (2006.01) |
| *G02B 21/16* | (2006.01) |
| *G02B 21/26* | (2006.01) |
| *H04N 5/225* | (2006.01) |
| *G01N 33/483* | (2006.01) |
| *G06K 9/03* | (2006.01) |
| *G06K 9/46* | (2006.01) |
| *G01N 15/00* | (2006.01) |
| *G01N 15/10* | (2006.01) |

(52) U.S. Cl.
CPC ..... *G01N 15/1463* (2013.01); *G01N 33/4833* (2013.01); *G01N 35/00029* (2013.01); *G01N 35/00871* (2013.01); *G02B 21/16* (2013.01); *G02B 21/26* (2013.01); *G06K 9/0014* (2013.01); *G06K 9/036* (2013.01); *G06K 9/4647* (2013.01); *G06K 9/4652* (2013.01); *G06K 9/4661* (2013.01); *H04N 5/2256* (2013.01); *B01L 2300/0654* (2013.01); *B01L 2300/0829* (2013.01); *B01L 2300/0851* (2013.01); *B01L 2300/0896* (2013.01); *B01L 2300/12* (2013.01); *G01N 2015/0065* (2013.01); *G01N 2015/1006* (2013.01); *G01N 2035/00148* (2013.01)

(58) Field of Classification Search
CPC ............... B01L 2300/12; B01L 3/5085; G01N 15/1425; G01N 15/1463; G01N 2015/0065; G01N 2015/1006; G01N 2035/00148; G01N 33/4833; G01N 35/00029; G01N 35/00871; G02B 21/16; G02B 21/26; G06K 9/0014; G06K 9/00147; G06K 9/036; G06K 9/4647; G06K 9/4652; G06K 9/4661; H04N 5/2256

See application file for complete search history.

(56) References Cited

U.S. PATENT DOCUMENTS

| | | | |
|---|---|---|---|
| 4,965,725 A | * 10/1990 | Rutenberg | G01N 15/1468 382/224 |
| 7,381,375 B2 | 6/2008 | Ravkin et al. | |
| 7,738,094 B2 | 6/2010 | Goldberg | |
| 9,366,628 B2 | 6/2016 | Crandall et al. | |
| 9,506,917 B2 | 11/2016 | Fan et al. | |
| 9,953,209 B2 | 4/2018 | Adalsteinsson et al. | |
| 2003/0082516 A1 | * 5/2003 | Straus | G01N 33/56916 435/4 |
| 2004/0102742 A1 | * 5/2004 | Tuyl | B01L 3/0268 604/298 |
| 2006/0008843 A1 | 1/2006 | Sachesenmeier et al. | |
| 2006/0013031 A1 | 1/2006 | Ravkin et al. | |
| 2006/0124870 A1 | 6/2006 | Bobanovic et al. | |
| 2006/0132779 A1 | 6/2006 | Hunt et al. | |
| 2006/0199168 A1 | * 9/2006 | Wills | A61K 35/12 435/4 |
| 2007/0291111 A1 | 12/2007 | Ladha | |
| 2009/0029378 A1 | * 1/2009 | Connelly | G01N 21/6428 435/6.14 |
| 2010/0126857 A1 | * 5/2010 | Polwart | B01L 9/527 204/403.14 |
| 2010/0173394 A1 | * 7/2010 | Colston, Jr. | B01F 3/0807 435/287.2 |
| 2011/0293611 A1 | * 12/2011 | Pearl | A61K 35/30 424/134.1 |
| 2013/0171096 A1 | * 7/2013 | Hsieh | C07K 16/22 424/85.2 |
| 2013/0242382 A1 | 9/2013 | Komuro | |
| 2014/0226866 A1 | 8/2014 | Crandall et al. | |
| 2014/0273194 A1 | * 9/2014 | Handique | G01N 33/4833 435/288.7 |
| 2016/0209319 A1 | 7/2016 | Adalsteinsson et al. | |
| 2016/0217315 A1 | 7/2016 | Adalsteinsson et al. | |
| 2016/0291049 A1 | * 10/2016 | Arumugam | G01N 35/1011 |
| 2016/0314583 A1 | * 10/2016 | Couch | G01N 33/574 |

OTHER PUBLICATIONS

Loginov, Denis, Development of High-Throughput Platforms for Single-Cell Analysis, Thesis, 90 pages, 2015.

Pla-Roca, M. et al., Addressable Nanowell Arrays Formed Using Reversibly Sealable Hybrid Elastomer-Metal Stencils, Anal. Chem. 82:3848-3855 (2010).

Written Opinion, PCT/US2016/013724 (Systems, Methods, and Apparatus for in Vitro Single-Cell Identification and Recovery, filed Jan. 15, 2016), issued by ISA/European Patent Office, 9 pages, dated Jul. 19, 2016.

* cited by examiner

# SYSTEMS, METHODS, AND APPARATUS FOR IN VITRO SINGLE-CELL IDENTIFICATION AND RECOVERY

CROSS-REFERENCE TO RELATED APPLICATIONS

This application is a Divisional Application of U.S. application Ser. No. 14/997,439, filed on Jan. 15, 2016, which claims the benefit of U.S. Provisional Application No. 62/104,036, filed Jan. 15, 2015, the contents of which are hereby incorporated by reference herein in their entireties.

GOVERNMENT SUPPORT

This invention was made with Government support under Grant Nos. R21 AI106025 and 1-R56-AI104274-01 awarded by the National Institutes of Health and under Contract No. W911NF-13-D-0001 awarded by the U.S. Army Research Office. The Government has certain rights in the invention.

FIELD OF THE INVENTION

The invention relates generally to systems and methods for in vitro single-cell identification and recovery (e.g., high throughput).

BACKGROUND

The last several decades have seen tremendous progress in the understanding of biological processes. Despite these advances, research in many important fields, such as immunology and cancer biology, has made it increasingly clear that bulk measurements can mask characteristics of individual cells or subsets of cells. Such individual cells and small subsets of cells may contribute significantly to biological processes, yet may not be identical to the population average measured by existing techniques. In addition, interactions between individual players may not be resolved if only an average behavior is studied. As a result, traditional methods may draw a misleading picture of dynamic responses of cells to the given perturbations of their biological environments, necessitating development of technologies for single-cell analysis. Moreover, inefficiencies in sample handling and data collection inherent in current flow-based profiling methods (e.g., flow cytometry) limit comprehensive phenotyping of the scarce cells recovered from tissue samples.

Conventional slide-based cytometry can efficiently provide capture of all cells in the sample in a first step, preventing cell loss during cell staining and data acquisition. However, current methods of acquiring images of the captured cells, such as laser scanning slide cytometry and multi-parameter confocal microscopy, have (1) lagged on the number of channels available on state-of-the art flow cytometers and (2) are costly, which restrict their availability primarily to core facilities. Moreover, while conventional methods using iterative staining have expanded the number of markers that can be detected, they are both labor and time intensive.

Further, typical slide-based cytometry methods require the cells to be fixed to the slide, thereby preventing further analysis of these precious cell samples using functional assays, which are critical for understanding the role of these cells in tissue-restricted immune responses.

There is a need for the development of efficient methodologies for interrogating cells (e.g., lymphocytes, leukocytes, tumor cells, stromal cells, neuronal cells, cell lines (e.g., CHO cells, NS0 cells), stem cells, embryos, and the like) present in scarce cell samples to advance understanding of clinical responses to the growing number of experimental interventions targeting tissue in the fields of cancer immunotherapy, autoreactive bowel disorders, allergy, infectious disease, multiple sclerosis, neuroimmunological disease, and HIV. Development of such methods must have the ability to image a large area for increased throughput, have a large spectral depth (e.g., 10-30 color channels for 10-30 markers), automatically scan large area for scarce cells, pick the scarce cells, and maintain cell viability for further functional characterization.

SUMMARY

Described herein are systems and methods for automatically identifying and recovering individual cells of interest from a sample of biological matter, e.g., a biological fluid, tumor biopsies, punch biopsies, skin samples, cytobrushes, lavages, fine needle aspirates, cerebrospinal fluid, synovial fluid, blood, sputum, urine, etc. Also described are methods of enriching a cell type of interest (e.g., lymphocytes, leukocytes tumor cells, stromal cells, neuronal cells, cell lines (like CHO cells, NS0 cells), stem cells, embryos, and the like). These systems and methods offer advantages over pre-existing systems in that they allow automated (or semi-automated) identification and recovery of individual cells at a high throughput. The systems and methods also allow for manual verification of automatically-identified candidate cells, which may be advantageous for satisfaction of certain regulatory requirements, while still allowing for high throughput.

The systems and methods described herein allow for coordinated performance of two or more of the following, e.g., all with the same device: cell enrichment, cell identification, individual cell recovery, and analysis (e.g., sequencing) of individual, recovered cells. Moreover, the systems and methods have the ability to (i) image large areas of tissue samples and biopsies for increased throughput, (ii) have a large spectral depth (e.g., 10-30 color channels for 10-30 markers), (iii) automatically scan large areas for scarce cells, (iv) pick the scarce cells, (v) maintain cell viability for further functional characterization (cells can be kept alive during processing), and/or (vi) provide dynamic and secretory measurements of individual cells. In contrast to conventional systems, which take days for identifying cell types and relevant information, these systems and methods can provide results and information in under 20 minutes.

As one example, circulating tumor cells (CTCs) are rare tumor cells found in the blood of cancer patients (~1 ppm mononuclear cells) and are believed to be responsible for disseminating cancer (metastasis). The numbers of CTCs found in blood can serve as a prognostic indicator in certain tumor types. CTCs offer many opportunities beyond enumeration. Indeed, molecular analysis of CTCs may reveal information about solid tumor lesions and allow monitoring of the progression of disease from blood samples. Along with the analysis of circulating tumor DNA, such "liquid biopsies" offer a real-time, minimally-invasive window into metastasis that would not be feasible using repeated surgical biopsies.

Sequencing-based analyses of CTCs allow the tracing of lineage-specific evolution of tumors, assessment of clonal heterogeneity, and identification of mechanisms of resistance to therapies. However, the inherently small amount of material available from each cell (e.g., only 1 copy of each parental allele) necessitates the use of amplification methods prior to sequencing that introduce biases and errors which confound the confident calling of mutations and copy-number alterations. Census-based methods enable accurate and powered calling of somatic alterations from CTCs, but require isolating, amplifying, and sequencing multiple independent CTCs, and thus are limited when an insufficient number of cells is available. As such, increasing the number of single CTCs recovered from a given volume of blood (or processing larger volumes in a given time) is paramount to performing more confident and detailed analyses, along with expanding the (sometimes incompatible) types of analysis performed on each sample.

In one aspect, the invention is directed to a multiscale deposition-well plate (e.g. for use with a system for automated identification and/or recovery of individual cells of interest as described herein) comprising one or more sample wells (e.g., from three to twenty, or from three to twelve) and zero or more recovery wells (e.g., 24, 48, 96, at least 24, at least 48, at least 96, etc.).

In certain embodiments, the multiscale deposition-well plate comprises a plurality (e.g., an array) of macro-scale wells (e.g., each macro-scale well with any one or more of length, width, and/or depth of at least 1 mm, at least 3 mm, at least 5 mm, or at least 8 mm, and/or with any one or more of length, width, and/or depth no greater than about 100 mm, no greater than about 50 mm, or no greater than about 25 mm), wherein each of the macro-scale wells comprise a plurality of micro-scale and/or nano-scale wells (e.g., each micro-scale well with any one or more of length, width, and/or depth of at least 1 µm, at least 5 µm, or at least 10 µm, and/or with any one or more of length, width, and/or depth no greater than about 1000 µm, no greater than about 500 µm, no greater than about 250 µm, or no greater than about 100 µm) (e.g., each nano-scale well with any one or more of length, width, and/or depth of at least 1 nm, at least 5 nm, or at least 10 nm, and/or with any one or more of length, width, and/or depth no greater than about 1000 nm, no greater than about 500 nm, no greater than about 250 nm, or no greater than about 100 nm) (e.g., wherein each micro-scale well contains no greater than about 1000 pL of sample volume, no greater than about 500 pL of sample volume, no greater than about 100 pL of sample volume, or no greater than about 50 pL of sample volume, or no greater than about 10 pL).

In certain embodiments, each of the wells has a sample-contacting surface compatible with cells (e.g., live cells) (e.g., e.g., lymphocytes, leukocytes, tumor cells, stromal cells, neuronal cells, cell lines (e.g., CHO cells, NS0 cells), stem cells, embryos, and the like), the sample-contacting surface comprising one or more members selected from the group consisting of glass, silicon, polymer (e.g., polycarbonate, polystyrene, epoxy, ABS plastics, polypropylene, or fluoropolymer), elastomer (e.g., polydimethylsiloxane), a thermoplastic, and a medical grade plastic.

In another aspect, the invention is directed to a deposition well-plate comprising one or more sample wells and one or more recovery wells, wherein the sample well(s) and recovery well(s) are positioned in proximity to each other (e.g. to require only minimal travel of a cell-recovery implement (e.g., needle) from a sample well to a recovery well, e.g., during the process of physical retrieving of a cell from a sample well to a recovery well) (e.g, wherein each sample well is within 100 mm, 50 mm, 25 mm, 10 mm, or 5 mm of the nearest recovery well).

In certain embodiments, at least one of the sample well(s) and/or at least one of the recovery well(s) is a multiscale deposition well. In certain embodiments, the deposition well-plate comprises one or more wash stations. In certain embodiments, at least one of the sample wells comprises tapered walls (e.g., tapered at least 1 degree from vertical, at least 2 degrees from vertical, at least 3 degrees from vertical, at least 5 degrees from vertical, at least 7 degrees from vertical, at least 10 degrees from vertical, or at least 15 degrees from vertical, e.g., to allow cell picking close to edges).

In another aspect, the invention is directed to a system for performing multispectral cytometry (e.g., multicolor slide cytometry), the system comprising a processor of a computing device coupled to computer memory and/or operable to execute a set of pre-defined instructions (e.g., run computer software) to perform one or more of (i) to (iv) as follows (e.g., performing any 1, 2, 3, or all 4 of (i) to (iv)) (e.g., wherein all of the one or more step (i) to (iv) are performed in no greater than 30 minutes, no greater than 10 minutes, or no greater than 5 minutes for a given imaging task): (i) automated image calibration (e.g., calibration of image of cells in a micro-/nano-/pico-well grid) based on one or more of (a) to (d): (a) a raw image, (b) a dark frame, (c) a flat field frame, and (d) an illumination field frame; (ii) micro-/nano-/pico-well grid identification; (iii) cell identification and/or data extraction using one or both of (e) and (f): (e) a segmentation thresholding technique in which the threshold is based (e.g., solely) on a distribution of detected background pixels; and (f) a signal-to-noise maximization technique in which an aperture (e.g., of from 5 to 8 pixels) is set within a defined cell area to minimize dilution of signal from a decrease of signal near the cell periphery, and (iv) spectral spillover compensation (e.g. using an in silico F-minus one technique, e.g., as described herein below).

In another aspect, the invention is directed to a system for performing spectral spillover compensation in multicolor slide cytometry, the system comprising at least one memory and a processor of a computing device communicatively coupled to the at least one memory, (e.g., the system also comprising an imaging device) wherein the processor is operable to perform one or more of steps (i) to (xi) as follows (e.g., performing any 1, 2, 3, 4, 5, 6, 7, 8, 9, 10, or 11 of steps (i) to (xi)): (i) identify location of one or more beads; (ii) extract a signal intensity of each pixel in each of a plurality of spectral channels (e.g., from 10 to 30 spectral channels) for each bead; (iii) create one or more 3D probability matrices relating intensity of signal in the spectral channel assigned to a fluorophore to the signal in each of the other channels; (iv) identify a location of cells in one or more images; (v) extract a signal in each of the plurality of spectral channels for each cell; (vi) extract a background signal (e.g., from one or more areas similar in size to an area from which a cell signal is extracted); (vii) determine an amount of each flurophore on each cell using one or more average spillover values extracted from the one or more probability matrices (e.g., and using standard linear compensation); (viii) create n-replicas of the compensated fluorophore content of each cell (e.g., in each replica, one fluorophore content is zeroed by replacing the value with a sample taken from the background signal distribution); (ix) sample at least one of the one or more 3D probability matrices to calculate an expected distribution of raw fluorescent signal in each channel based on concentration of each fluorophore; (x) compensate reconstructed pseudo-raw fluorescent values to create a distribution of calculated signal on cells identified as having no actual fluorophores present (e.g., population-level in silico FMOs); and (xi) resample a plurality of times (e.g., from 5 k to 100 k, or from 10 k to 100 k, or from 10 k to 1M times) for each cell to generate an expected negative cell distribution for each individual cell (e.g., single cell in silico FMOs).

In certain embodiments, the processor is operable to perform step (iii) (create the one or more 3D probability matrices) by performing (a) to (e), as follows: (a) determine an average amount of light emitted in channel B by fluorophore A (e.g., through linear regression); (b) normalize B signal to 0 (e.g., by subtracting a product fluorophore A concentration and slope of the linear regression in step (a)); (c) bin data into overlapping bins based on fluorophore A concentration; (d) create a 2D probability distribution of B signal for each bin (e.g., normalized to 1); and (e) combine the 2D distributions into a 3D spectral probability matrix.

In another aspect, the invention is directed to a system for hardware triggering of light sources for image acquisition (e.g., in multicolor cytometry, e.g., multicolor slide cytometry), the system comprising: a computer with processor operable (e.g., programmed) to: transmit spatial positions to a memory of a Stage, and filter positions to a memory of a Filter Wheel; transmit one or other parameters of acquisition to a microcontroller (e.g., wherein the one or more parameter comprises a number of positions and/or spectral channels to be acquired, one or more Light Source(s), exposure times, and/or Filter Wheel movements set for each channel), wherein the microcontroller is operable to start a cycle of image acquisition by signaling the Stage to move to a next position stored in its memory, wherein the Stage moves to the stored position and signals the microcontroller upon completion of the move, wherein the microcontroller signals the Filter Wheel to move to the next position stored in its memory, after which the Filter Wheel moves to the stored position and signals the microcontroller upon completion of the move, upon which the microcontroller signals the Light Source(s) to turn it/them on, then signals a Detector to begin integration of light, and upon completion of exposure time, the microcontroller is operable to signal the Light Source(s) to turn them off, after which the microcontroller signals the Detector to stop its integration, and the Detector automatically transfers an accumulated image to a frame grabber on the computer (e.g., and repeating steps for remaining spectral channels in the current spatial position), after which the microcontroller is operable to start the next cycle of image acquisition (e.g., by signaling movement of the stage to the next position).

In certain embodiments, the system comprises an optical train comprising a demagnification lens (e.g., to optimize resolution for cytometry and increase imaging speed).

In another aspect, the invention is directed to a system for automated identification and/or recovery (e.g., picking and deposition) of individual cells of interest, the system comprising a microscope comprising a light source, an optical train, and a detector capable of imaging a deposition-well plate (e.g., the multiscale deposition-well plate of any one of claims 1 to 7) positioned on a motorized stage (e.g., the system capable of imaging in one or more fluorescent channels (e.g., up to 10, up to 20, up to 30, up to 40, from 10 to 20, from 10 to 30, or from 10 to 40)).

In certain embodiments, the processor is operable to perform one or more of steps (i) to (v) of claim 8. In certain embodiments, the processor is operable to perform one or more of steps (i) to (xi) of claim 9.

In certain embodiments, the system further comprises elements for hardware triggering of light sources (e.g., as in claim 12).

In certain embodiments, the system is capable of performing an imaging run with at least 12 channels (e.g., at least 12 channels, at least 16 channels, or at least 23 channels) in a total time less than 150 minutes (e.g., less than 100 minutes, less than 75 minutes, less than 50 minutes, less than 40 minutes, less than 30 minutes, less than 25 minutes, less than 20 minutes, less than 15 minutes, less than 10 minutes, or less than 5 minutes), where the total imaged area is at least 1000 mm$^2$.

In another aspect, the invention is directed to a method comprising using any one of the above-described systems to perform an imaging run with at least 12 channels (e.g., at least 12 channels, at least 16 channels, or at least 23 channels) in a total time less than 150 minutes (e.g., less than 100 minutes, less than 75 minutes, less than 50 minutes, less than 40 minutes, less than 30 minutes, less than 25 minutes, less than 20 minutes, less than 15 minutes, less than 10 minutes, or less than 5 minutes), where the total imaged area is at least 1000 mm$^2$.

In another aspect, the invention is directed to a method of performing multispectral cytometry (e.g., multicolor slide cytometry), the method comprising performing one or more of steps (i) to (iv) as follows (e.g., performing any 1, 2, 3, or all 4 of (i) to (iv)) (e.g., wherein all of the one or more steps (i) to (iv) are performed in no greater than 30 minutes, no greater than 10 minutes, or no greater than 5 minutes for a given imaging task): (i) performing, by a processor of a computing device, automated image calibration (e.g., calibration of image of cells in a micro-/nano-/pico-well grid) based on one or more of (a) to (d): (a) a raw image, (b) a dark frame, (c) a flat field frame, and (d) an illumination field frame; (ii) performing, by the processor, micro-/nano-/pico-well grid identification; (iii) performing, by the processor, cell identification and/or data extraction using one or both of (e) and (f): (e) a segmentation thresholding technique in which the threshold is based (e.g., solely) on a distribution of detected background pixels; and (f) a signal-to-noise maximization technique in which an aperture (e.g., of from 5 to 8 pixels) is set within a defined cell area to minimize dilution of signal from a decrease of signal near the cell periphery and (iv) performing, by the processor, spectral spillover compensation (e.g. using an in silico F-minus one technique, e.g., as described in claim 20).

In another aspect, the invention is directed to a method for performing spectral spillover compensation in multicolor slide cytometry, the method comprising performing one or more of steps (i) to (xi) as follows using a processor of a computing device (e.g., performing any 1, 2, 3, 4, 5, 6, 7, 8, 9, 10, or all 11 of steps (i) to (xi)): (i) identifying location(s) of one or more beads; (ii) extracting a signal intensity of each pixel in each of a plurality of spectral channels (e.g., from 10 to 30 spectral channels) for each bead; (iii) creating one or more 3D probability matrices relating intensity of signal in the spectral channel assigned to a fluorophore to the signal in each of the other channels; (iv) identifying a location of cells in one or more images; (v) extracting a signal in each of the plurality of spectral channels for each cell; (vi) extracting a background signal (e.g., from one or more areas similar in size to an area from which a cell signal is extracted); (vii) determining an amount of each flurophore on each cell using one or more average spillover values extracted from the one or more probability matrices (e.g., and using standard linear compensation); (viii) creating n-replicas of the compensated fluorophore content of each cell (e.g., in each replica, one fluorophore content is zeroed by replacing the value with a sample taken from the background signal distribution); (ix) sampling at least one of the one or more 3D probability matrices to calculate an expected distribution of raw fluorescent signal in each channel based on concentration of each fluorophore; (x) compensating reconstructed pseudo-raw fluorescent values to create a distribution of calculated signal on cells identified as having no actual fluorophores present (e.g., population-level in silico FMOs); and (xi) resampling a plurality of times (e.g., from 5 k to 100 k, or from 10 k to 100 k, or from 10 k to 1M times) for each cell to generate an expected negative cell distribution for each individual cell (e.g., single cell in silico FMOs).

In another aspect, the invention is directed to a method for hardware triggering of light sources for image acquisition (e.g., in multicolor cytometry, e.g., multicolor slide cytometry), the method comprising: transmitting, by a processor of a computing device, spatial positions to a memory of a Stage, and filter positions to a memory of a Filter Wheel; transmitting, by the processor, one or other parameters of acquisition to a microcontroller (e.g., wherein the one or more parameter comprises a number of positions and/or spectral channels to be acquired, one or more Light Source(s), exposure times, and/or Filter Wheel movements set for each channel); starting, by the microcontroller, a cycle of image acquisition by signaling the Stage to move to a next position stored in its memory, wherein the Stage moves to the stored position and signals the microcontroller upon completion of the move; signaling, by the microcontroller, the Filter Wheel to move to the next position stored in its memory, after which the Filter Wheel moves to the stored position and signals the microcontroller upon completion of the move; signaling, by the microcontroller, the Light Source(s) to turn it/them on, then signaling a Detector to begin integration of light, and upon completion of exposure time, signaling, by the microcontroller, the Light Source(s) to turn them off; signaling, by the microcontroller, the Detector to stop its integration; automatically transferring an accumulated image from the Detector to a frame grabber (e.g., and repeating steps for remaining spectral channels in the current spatial position); and beginning, by the microcontroller, a subsequent cycle of image acquisition (e.g., by signaling movement of the stage to the next position).

In another aspect, the invention is directed to a system for automated identification and recovery of individual cells of interest, the system comprising: a microscope comprising a light source, an optical train, and a detector capable of imaging a deposition—well plate positioned on a motorized stage (e.g., capable of imaging in one or more fluorescent channels); a motorized stage and a set of actuators configured to translate the stage in a first direction and a second direction in a horizontal plane (e.g., wherein translation of the stage is constrained to an x-y plane); a motorized focus drive to translate an optical objective of the microscope in a vertical direction (e.g., z-direction); a micromanipulator arm comprising an actuator configured for constrained movement of the micromanipulator arm in the vertical direction (e.g., z-direction) and optionally in two other dimensions (e.g., x-y plane) to calibrate a location of a capillary needle within an imaging field of view of the detector, wherein the capillary needle is removably fastened/fastenable to the micromanipulator arm and oriented in the vertical direction; optionally, an electronically-controlled micropumping system (e.g., liquid displacement and other types of pumps for manipulation of small volumes of fluid) comprising pumps (e.g., positive and negative pressure pumps, e.g., displacement pumps, e.g., velocity, gravity, other actuation types of pumps) and valves (e.g., for manipulating nano- to microliter volumes of fluid, e.g., for introduction of a volume of fluid comprising each individual cell of interest into the capillary needle and/or for release of the volume of fluid thereby depositing each individual cell of interest into a first recovery well of one or more recovery wells); one or more deposition-well plates comprising one or more sample wells (e.g., 3-12) and/or one or more recovery wells (e.g., 24, 48, 96, etc.), wherein the deposition-well plates are removably attached/attachable to the motorized stage; an optional electromechanical arm for automated introduction of deposition plates onto the stage; and a processor of a computing device, wherein the processor is configured to send a series of control signals to cause: (i) the microscope to capture an image of a first sample well, wherein the processor is further configured to analyze the image to identify a location of an individual cell of interest within the first sample well; (ii) the set of actuators to translate the motorized stage (e.g., in the horizontal plane and the motorized focus drive in the vertical direction) according to the identified location of the individual cell of interest within the first sample well, such that the capillary needle is oriented above the individual cell of interest; (iii) the actuator to translate, in the vertical direction and optionally in the horizontal plane, the micromanipulator arm to orient a tip of the capillary needle in the first sample well at or sufficiently near the individual cell of interest; (iv) introduction of a volume of fluid comprising the individual cell of interest into the capillary needle; (v) the actuator to translate, in the vertical direction and optionally in the horizontal plane, the micromanipulator arm such that the capillary needle containing the volume of fluid comprising the individual cell of interest is raised out of the first sample well; (vi) the set of actuators to translate the motorized stage, such that the capillary needle containing the volume of fluid comprising the individual cell of interest is oriented above the first recovery well; (vii) the actuator to translate, in the vertical direction and optionally in the horizontal plane, the micromanipulator arm such that the capillary needle containing the volume of fluid comprising the individual cell of interest is lowered into the first recovery well; and (viii) a release of the volume of fluid thereby depositing the individual cell of interest into the first recovery well.

In certain embodiments, the capillary needle is (or comprises) steel (e.g., surgical steel, stainless steel, etc.), glass, or plastic. In certain embodiments, the system further comprises: a back-light illumination system co-located with the micromanipulator arm and capillary needle and oriented to project light such that the microscope collects sufficient transmitted light to image and analyze the individual cell of interest in this channel.

In certain embodiments, the processor is further configured to perform a multi-point calibration of a surface of the deposition-well plate to correct spatial (e.g., rotational or deformational) variations in three-dimensional space, thereby providing a coordinate system enabling the microscope stage and the motorized focus drive to be automatically translated by the processor. In certain embodiments, the multi-point calibration comprises positioning the motorized stage at positions corresponding to one or more locations of an imaging region of the deposition-well plate; identifying coordinates corresponding to these locations; and using the coordinates to extrapolate one or more points corresponding to one or more additional positions within the imaging region, respectively, thereby correcting for spatial (e.g., rotational or deformational) variations of the deposition-well plate. In certain embodiments, the processor is configured to perform automated search for specific points on the deposition-well plate using a software image analysis algorithm to detect the specific points. In certain embodiments, the processor is configured to perform multi-point calibration of imaging focus at one or more select locations of the deposition-well plate using a software autofocus algorithm comprising a focus scoring method (e.g., variance of laplacian method or normalized variance method) and a one-dimensional root-finding algorithm (e.g., Brent's minimization algorithm), and extrapolating the multi-point calibration for a plurality of other locations of the deposition-well plate (e.g., performed automatically by the microscope based on one or more absolute positions of the stage, e.g., post-initialization, e.g., where position of the deposition-well plate is fixed with respect to the stage).

In certain embodiments, the processor is configured to determine a spatial (e.g., vertical) position of the tip of the capillary needle based on one or more needle (e.g., position, e.g., height) calibration images (e.g., an autofocus image) (e.g., thereby obviating the need for a manual recalibration after a capillary needle change).

In certain embodiments, the introduction of the volume of fluid comprising the individual cell of interest into the capillary needle and the release of the individual cell of interest into the first recovery well are conducted with or without a working fluid (e.g., silicon oil), and/or with or without a micropump. In certain embodiments, the introduction of the volume of fluid comprising the individual cell of interest into the capillary needle and the release of the individual cell of interest into the first recovery well are further controlled by the processor based on an image analysis algorithm (e.g., a particle-tracking algorithm) and spatial data structure (e.g., k-d tree data structure) designed to trace locations of individual cells on the first recovery well and/or the capillary needle.

In certain embodiments, the individual cell of interest is a member selected from the group consisting of a circulating tumor cell (CTC), a lymphocyte, a leukocyte, a tumor cell, a stromal cell, a neuronal cell, a cell line (e.g., a CHO cell, a NS0 cell), a stem cell, and an embryo.

In certain embodiments, the system comprises a module ("Nanobox") to automatically identify candidate individual cells of interest (e.g., based on morphology and a pre-defined set of fluorescence intensity thresholds), present the images of candidate cells (e.g., in transmitted and fluorescent light channels) to a user for manual review (e.g., assisted by a machine learning algorithm), and automatically transfer the chosen cells into recovery wells (e.g., at a rate of 100-1000 cells per hour) (e.g., one cell at a time). In certain embodiments, the system is further configured to: detect and present dynamic behaviors of individual cells of interest based on images taken at multiple time points; trace the locations of individual cells of interest over time (including time to transfer the chosen cells into recover wells); and resolve potential duplicates amongst candidate cells of interest due to an overlap between adjacent images (e.g., using an image analysis algorithm and k-d tree algorithm).

In certain embodiments, the processor is further configured with a module (e.g., a built-in module or a stand-alone module) to define an optimal set of fluorescence intensity thresholds based on statistical and/or visual analysis performed simultaneously with loading and processing of images; and/or to simultaneously present the images under screen cursor in all channels and mark by a user locations of true positive individual cells of interest that are either detected correctly or missed by the processor (e.g., to facilitate transfer of chosen cells of interest into recovery wells, e.g., to teach a machine learning algorithm to suggest individual cells of interest).

In another aspect, the invention is directed to a method of enriching a cell type of interest, the method comprising: processing (e.g., lysing) a sample of biological fluid (e.g., blood, plasma, urine, sputum, saliva, amniotic fluid, cerebrospinal fluid, etc.), thereby forming a cell suspension; incubating the cell suspension with immunomagnetic beads configured to selectively label a cell type of interest (e.g., circulating tumor cells), thereby forming a biological fluid comprising a bead-labeled cell suspension; dispensing the biological fluid upon a biocompatible dense medium (e.g., Percoll™, e.g., a colloidal suspension of silica nanoparticles coated with polyvinylpyrrolidone), thereby forming a layered fluid comprising a biological fluid layer and a biocompatible dense medium layer; causing the labeled cells to settle into the biocompatible dense medium layer (e.g., waiting sufficient time for gravity to settle the labeled cells, e.g. placing a magnet underneath the biocompatible dense medium); and aspirating the biological fluid layer (e.g., substantially removing the cells of the biological fluid which are not the cell type of interest.

In certain embodiments, causing the labeled cells to settle substantially beneath the biocompatible dense medium layer comprises introducing a magnetic field beneath the biocompatible dense medium layer, thereby forcing the labeled cells into the biocompatible dense medium layer (e.g., down to a bottom of a recovery well containing the biological fluid layer and the biocompatible dense medium layer). In certain embodiments, the method comprises washing and staining the labeled cells.

In certain embodiments, the biological fluid is a member selected from the group consisting of blood, plasma, urine, sputum, saliva, amniotic fluid, bone marrow aspirate, fine-needle aspirate (e.g., or other small tissue biopsies), whipple, and cerebrospinal fluid. In certain embodiments, the biological fluid is blood and the cell type of interest is circulating tumor cells.

In another aspect, the invention is directed to a method for automated identification and recovery of individual cells of interest, the method comprising: capturing, by a detector (e.g., a detector of a microscope), an image of a first sample well; analyzing, by a processor of a computing device, the image to identify a location of an individual cell of interest within the first sample well; automatically translating a motorized stage in a first direction and/or a second direction in a horizontal plane (e.g., the x-y plane), and a focus drive in a third direction perpendicular to a horizontal plane (e.g., the z plane), according to the identified location of the individual cell of interest within the first recovery well, such that a capillary needle removably fastened to a micromanipulator arm is oriented above the individual cell of interest; automatically translating, in a vertical direction, and optionally in the horizontal plane, the micromanipulator arm to orient a tip of the capillary needle in the first sample well at or sufficiently near the individual cell of interest; introducing a volume of fluid comprising the individual cell of interest into the capillary needle; automatically translating, in the vertical direction, the micromanipulator arm such that the capillary needle containing the volume of fluid comprising the individual cell of interest is raised out of the first sample well; translating the microscope stage, such that the capillary needle containing the volume of fluid comprising the individual cell of interest is oriented above a first recovery well; automatically translating, in the vertical direction and optionally in the horizontal plane, the micromanipulator arm to orient a tip of the capillary needle at a sufficient height above the bottom of the first recovery well; and releasing the volume of fluid thereby depositing the individual cell of interest into the first recovery well.

In certain embodiments, the method further comprises detecting and presenting dynamic behaviors of individual cells of interest based on images taken at multiple time points; tracing the locations of individual cells of interest over time (including time to transfer the chosen cells into recovery wells); and resolving potential duplicates amongst candidate cells of interest due to an overlap between adjacent images (e.g., using an image analysis algorithm and k-d tree algorithm).

In certain embodiments, the method further comprises: defining an optimal set of fluorescence intensity thresholds based on statistical and/or visual analysis performed simultaneously with loading and processing of images; and/or simultaneously presenting the images under screen cursor in all channels and marks by a user locations of true positive individual cells of interest that are either detected correctly or missed by the processor (e.g., to facilitate transfer of chosen cells of interest into recovery wells, e.g., to teach a machine learning algorithm to suggest individual cells of interest).

In certain embodiments, the detector (e.g., microscope) and/or the processor comprises a module for: automatically scanning (e.g., using a low-magnification objective) and register 1- and/or 2-dimensional barcodes printed by a plate manufacturer at the bottom and/or a side wall of the recovery wells and/or recovery well plates; associating individual cells of interest with such wells and plates; and storing such associations either directly in or in a format compatible with a database.

In another aspect, the invention is directed to a deposition-well plate comprising one or more sample wells (e.g., 3-12) and one or more recovery wells (e.g., 24, 48, 96, etc.).

In certain embodiments, the deposition-well plate additionally comprises one or more (e.g., 1-3) washing wells (e.g., containing a washing or lysis buffer) (e.g., to wash the tip of the capillary needle between each cell picking event). In certain embodiments, the one or more washing wells are located on a separate dedicated well-plate or integrated as part of the system.

In certain embodiments of the above-described systems, the processor is configured to automatically determine a success of transfer of cells using an image processing algorithm performed on images taken before and after handling of cells with the capillary needle.

It is contemplated that where embodiments are described with respect to one aspect of the invention, they may also apply with respect to other aspects of the invention.

Definitions

"Detector": As used herein, the term "detector" includes any detector of electromagnetic radiation including, but not limited to, EMCCD camera, CMOS camera, photomultiplier tubes, photodiodes, and avalanche photodiodes.

"Substantially": As used herein, the term "substantially", and grammatical equivalents, refer to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result.

Figures are presented herein for illustration purposes only, not for limitation.

It is contemplated that methods, systems, and processes described herein encompass variations and Drawings are presented herein for illustration purposes, not for limitation.

BRIEF DESCRIPTION OF THE DRAWINGS

The foregoing and other objects, aspects, features, and advantages of the present disclosure will become more apparent and better understood by referring to the following description taken in conduction with the accompanying drawings, in which.

DETAILED DESCRIPTION

Figure 1A:
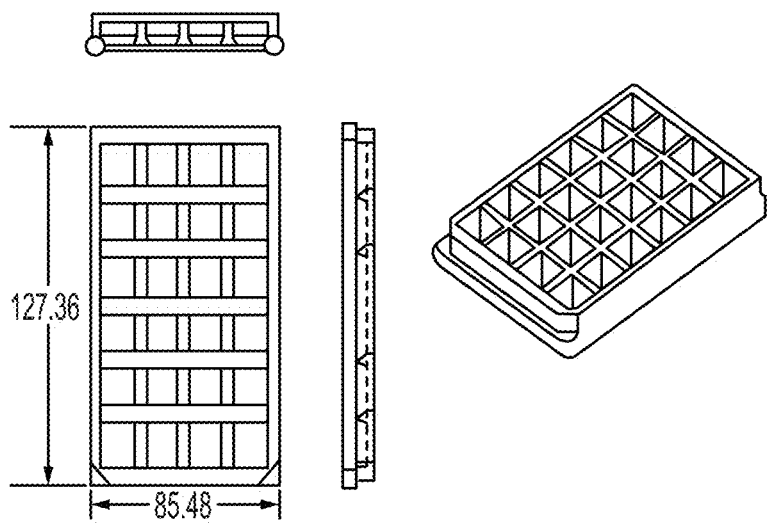
FIG. 1A shows compartmentalization of multiple samples on a single plastic device using an array of macroscopic wells ("macrowells").

Throughout the description, where compositions are described as having, including, or comprising specific components, or where methods are described as having, including, or comprising specific steps, it is contemplated that, additionally, there are compositions of the present invention that consist essentially of, or consist of, the recited components, and that there are methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Headers are used herein to aid the reader and are not meant to limit the interpretation of the subject matter described.

Described herein are systems and methods for automatically identifying and recovering individual cells of interest from a sample of biological matter, e.g., a biological fluid, tumor biopsies from fine needle aspirates, cerebrospinal fluid, blood, sputum, saliva, amniotic fluid, cerebrospinal fluid, urine, etc. Also described are methods of enriching a cell type of interest. Cells of interest include, but are not limited to lymphocytes, leukocytes tumor cells, stromal cells, neuronal cells, cell lines (like CHO cells, NS0 cells), stem cells, embryos, and the like.

These systems and methods offer advantages over pre-existing systems in that they allow automated (or semi-automated) identification and recovery of individual cells at a high throughput. The systems and methods also allow for manual verification of automatically-identified candidate cells, which may be advantageous for satisfaction of certain regulatory requirements, while still allowing for high throughput. Moreover, the systems and methods described herein allow for coordinated performance of two or more of the following, e.g., all with the same device: cell enrichment, cell identification, and individual cell recovery for further analysis (e.g., sequencing) of individual, recovered cells.

Further advantages compared to conventional methods include (1) maintenance of viability of small clinical samples (e.g., samples are not dissolved or degraded during measurements; cells are not destroyed, permeabilized or rendered non-viable), (2) increased sensitivity due to viability, and (3) ability to perform additional measurements to aggregate data (e.g., kinetics, cytolysis, motility, proliferative capacity, growth, secretion, functional assays) to determine which cells are of interest.

In one example, circulating tumor cells (CTCs) are rare tumor cells found in the blood of cancer patients (~1 ppm mononuclear cells) and are believed to be responsible for disseminating cancer (metastasis). The numbers of CTCs found in blood can serve as a prognostic indicator in certain tumor types. CTCs offer many opportunities beyond enumeration. Indeed, molecular analysis of CTCs may reveal information about solid tumor lesions and allow monitoring of the progression of disease from blood samples. Along with the analysis of circulating tumor DNA, such "liquid biopsies" offer a real-time, minimally-invasive window into metastasis that would not be feasible using repeated surgical biopsies.

Sequencing-based analyses of CTCs allow the tracing of lineage-specific evolution of tumors, assessment of clonal heterogeneity, and identification of mechanisms of resistance to therapies. However, the inherently small amount of material available from each cell (e.g., only 1 copy of each parental allele) necessitates the use of amplification methods prior to sequencing that introduce biases and errors which confound the confident calling of mutations and copy-number alterations. Census-based methods enable accurate and powered calling of somatic alterations from CTCs, but require isolating, amplifying, and sequencing multiple independent CTCs, and thus are limited when an insufficient number of cells is available. As such, increasing the number of single CTCs recovered from a given volume of blood (or processing larger volumes in a given time) is paramount to performing more confident and detailed analyses, along with expanding the (sometimes incompatible) types of analysis performed on each sample.

Deposition Wells

Arrays of micro-, nano-, or pico-wells offer a solution for compartmentalization of single cells for high-content multi-dimensional analysis of such samples. This technology enables correlation of multiple measurements involving both phenotype and genotype that can be performed either on-chip or off-chip in a single pipeline, establishing a platform for integrative single-cell analysis. Presented herein is a micro-, nano-, or pico-well platform for high-throughput cytometry and recovery of rare single cells that offers significant improvements in all these directions and has direct implications for preclinical and clinical research.

To accommodate increased numbers of samples processed in each modular operation, and expand compatibility with automated equipment used for these operations (e.g., liquid handlers, robotic macro- and micromanipulators, optical equipment, etc.), a new array is presented herein that relies on the form factor of the microtiter plates. This standard—SBS format (named after the Society for Biomolecular Screening)—provides compartmentalization of multiple samples on a single plastic device using an array of macroscopic wells ("macrowells") (FIG. 1A).

Figure 1B:
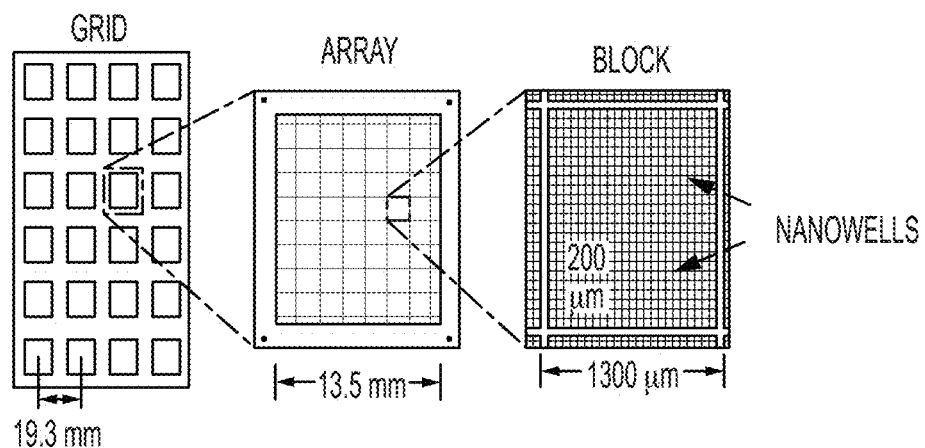
FIG. 1B shows arrays of microscopic wells (henceforth referred to as "nanowells" because of their sub-nanoliter volume) arranged in a grid matched to the arrangement of the macroscopic wells.
Figure 1C:
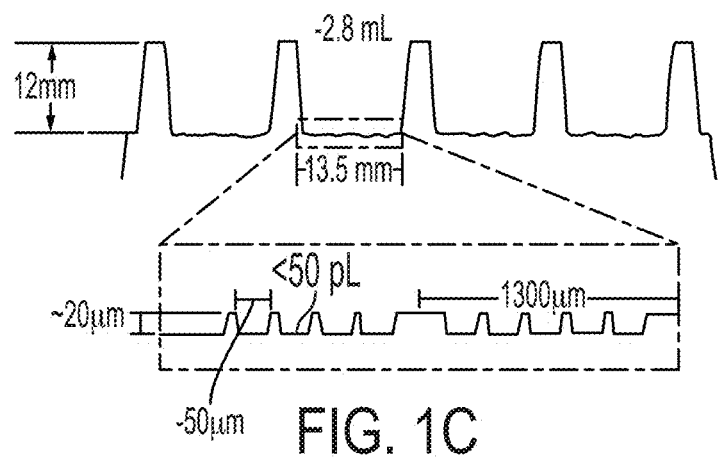
FIG. 1C shows that each array of nanowells resides at the bottom of a macrowell and allows for microscopic compartmentalization of cells from the corresponding sample.

In certain embodiments, the second part of the device comprises arrays of microscopic wells (henceforth referred to as "nanowells" because of their sub-nanoliter volume) arranged in a grid matched to the arrangement of the macroscopic wells (FIG. 1B). Each array of nanowells resides at the bottom of a macrowell and allows for microscopic compartmentalization of cells from the corresponding sample (FIG. 1C). These wells can comprise glass, silicon, polymers (polycarbonate, polystyrene, epoxy, ABS plastics, polypropylene, fluoropolymers), elastomers (polydimethylsiloxane), thermoplastics, or other common medical grade plastics or other materials compatible with cells.

Both parts of the device can be manufactured independently of each other, allowing additional flexibility not readily achieved with a single-piece geometry. It is possible to ensure that each part is reliably manufactured according to its specific set of dimensions and tolerances, which are vastly different for the macro- and the microscale. To demonstrate the utility of these devices prior to mass manufacturing, a number of rapid prototyping tools can be used that are suitable for the production of each part. These tools allow one to produce dozens of devices in rapid iterations to evaluate and achieve an optimal set of geometries. For example, 3D printing and stereolithography (SLA) are fast, accessible, and relatively inexpensive additive technologies for building macroscopic pieces where high resolution is not required. The microscopic part can be replicated, for example, with soft embossing from a rigid master that is fabricated once in a standard cleanroom facility.

Figure 2A:
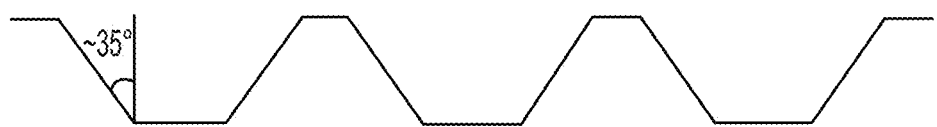
FIGS. 2A-2B show microfabrications of nanowells with tapered walls that is optimal for cell recovery and manufacturing, as compared to standard nanowells with vertical walls.
Figure 2B:
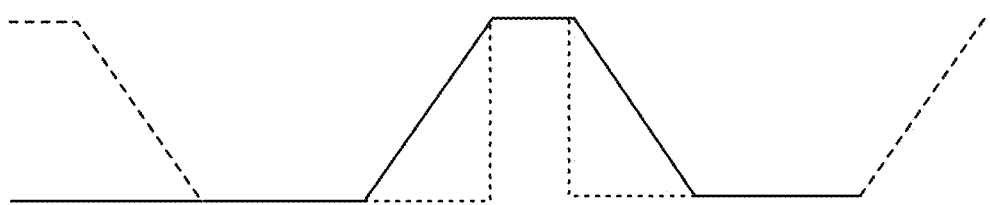

In certain embodiments, anisotropic etching of Si can be used for the microfabrication of a master for molding nanowells with tapered walls. This geometry facilitates replication of the rigid master in a subsequent molding step, as the draft angle of ~35° (defined by crystalline planes in Si), along with an extremely low surface roughness produced by the process, aid separation of the molded piece from the master (FIG. 2A). Additionally, such wells can be moved closer to each other, while maintaining the overall thickness and rigidity of the walls in between, which may otherwise deform or collapse upon replication in plastic had the walls been vertical (e.g. for 10 µm nominal width and 20-35 µm depth of the walls); see FIG. 2B for comparison. Close separation between the wells maximizes the useful area of the device (allowing more wells to fit in a smaller area), increasing the number of samples that can be processed on each device, decreasing imaging times per sample and minimizing cell loss due to the "dead" area (so that a larger proportion of cells could settle into the wells from suspension). In certain embodiments, bulk micromachining of Si is employed, ensuring that microscopic features are a single piece with the wafer, unlike in processes where the features are attached to the wafer and may wear out with repeated moldings (an example of such process is patterning of SU-8 posts). Other bulk micromachining methods may be employed (e.g., deep reactive-ion etching—DRIE), provided they are optimized for tapered walls (but may have a different angle).

In certain embodiments, to facilitate image acquisition and analysis, the nanowells are arranged in blocks that fit the field of view on the microscope; if the blocks were spaced further apart, the separation area would be unused in cell loading (potentially resulting in cell loss), while a shorter distance between the blocks would increase the number of blocks per given area, thus increasing the time spent on imaging and the risk of overexposure of sensitive fluorophores. As many wells as possible may be fit within each block, while accounting for a possible drift of the microscope stage from one block to another, which can lead to incomplete imaging of the outermost wells.

In certain embodiments, to reduce cell loss, the edges of each array of nanowells (corresponding to one macrowell) are designed to be as close as possible to the edges of the macrowell. However, since the two parts of the final device have different tolerances on the materials and processes involved in their production, and they have to be aligned and bonded, it is not always possible to rely on a microscopically precise alignment. As such, in certain embodiments, a ~200 µm border gap is introduced at the edges of each array. Additionally, to be able to access the outermost wells with macroscopic tools such as a liquid handling pipette or a cell picking capillary, as well as to facilitate molding of the macrowell plate in the future, a taper may be introduced to the sidewalls of each macrowell. In certain embodiments, macrowells and corresponding grids of blocks of nanowells may have geometries other than rectangular (e.g., circular) to improve compatibility with existing materials and methods specified by the SBS standards (e.g., those for 24 or 96-well plates). In certain embodiments geometries other than those compatible with standard 24-well or 96-well flat bottom plates are used.

Workflow

Figure 3:
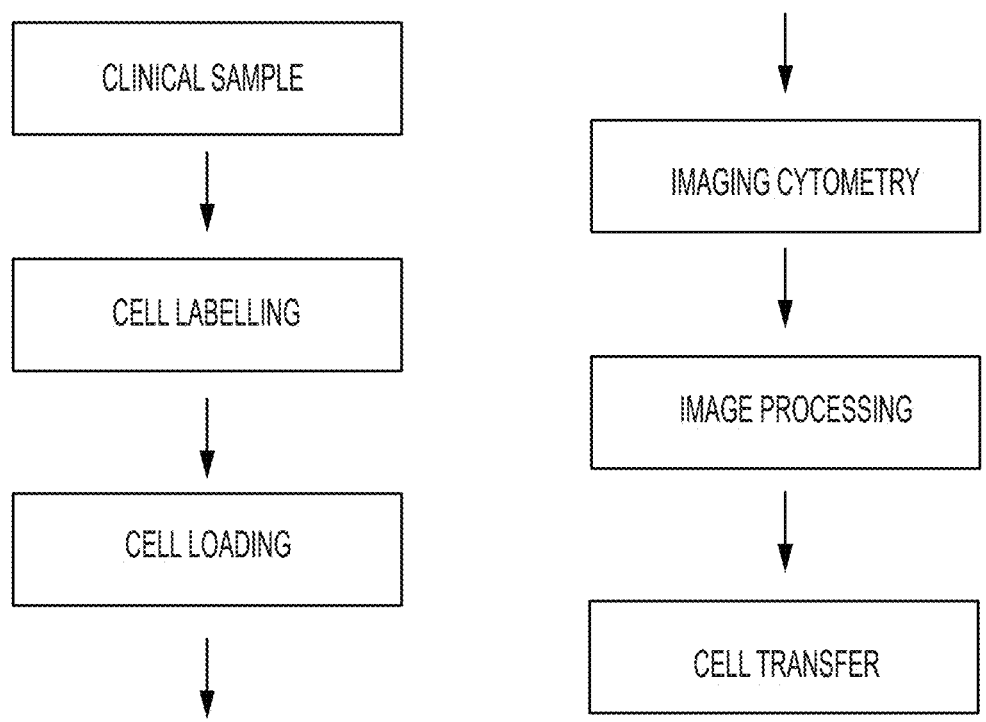
FIG. 3 shows an exemplary workflow using deposition plates for cell isolation, imaging, identification, and recovery.

An exemplary workflow for nanowell devices is illustrated in FIG. 3. The workflow starts with fluorescently labeling a suspension of cells drawn from a clinical sample (this could be a disaggregated tumor, a tissue biopsy, whole blood, etc.). The clinical sample may be optionally pre-enriched for the cells of interest by application of an external method (e.g. immunomagnetic enrichment or label-free sorting). Cells are then loaded from each suspension into the bottom of a corresponding macrowell (and optionally, into the nanowells at the bottom of the macrowells), which is accomplished in any of a number of ways (e.g., settling by gravity, centrifugation, immunomagnetic enrichment etc.). The workflow then proceeds with automated imaging of each well in a block-by-block fashion, and the results are processed with automated or semi-automated image analysis software (e.g., using the cytometry module by the processor). This analysis automatically produces a list of candidate cells (e.g., requiring manual confirmation), along with their associated locations, which can then be used to transfer individual cells of interest to the wells of a multiwell deposition plate (e.g., a 96-well plate) for downstream analysis (e.g., biochemical analysis, metabolites, transcriptional profiling, targeted sequencing, single-cell RNA sequencing, whole exome sequencing, epigenetic measurements (e.g., methylation, histones, chromatin), whole genome sequencing, or clonal expansion).

Immunomagnetic Enrichment

Various cells of interest may be identified and recovered, such as circulating tumor cells (CTCs). After the sample is enriched and cells are identified, they may still need to be recovered for further analysis. The new format of the deposition plates is leveraged to integrate enrichment with the automated platform established for cell identification and recovery.

Figure 4:
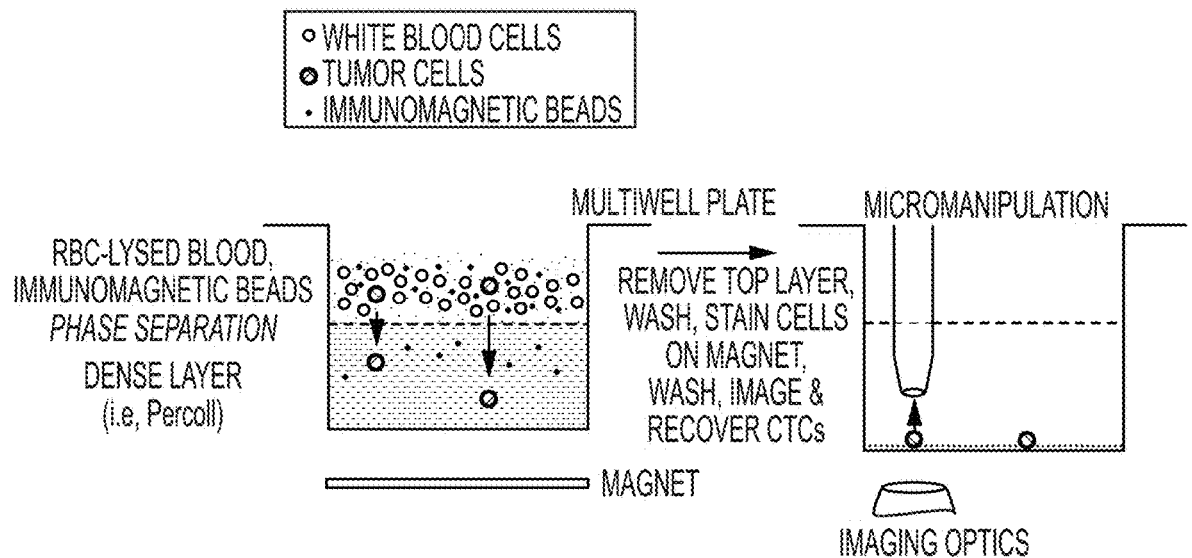
FIG. 4 shows a method for on-plate enrichment that combines immunomagnetic labeling with density gradients.

A method for on-plate enrichment is presented that combines immunomagnetic labeling with density gradients (FIG. 4). Lysis of contaminating cells such as red blood cells (RBCs) is performed on a vial of blood, and the resulting cell suspension is then incubated with immunomagnetic beads to selectively label selection marker-expressing cells (e.g., EpCAM-expressing CTCs). Macrowells of the plates are filled with a biocompatible dense medium such as Percoll™ (a colloidal suspension of silica nanoparticles coated with polyvinylpyrrolidone), and the bead-labeled cell suspension is dispensed on top of it; the two liquids remain separated according to their densities. Since the beads are much heavier than the cells or the medium (e.g., iron has 6-7 times higher density), and a few of them are conjugated to each cell, they can pull labeled cells through the dense layer by gravity. Additionally (or alternatively), these cells can be pulled with a magnet placed underneath the imaging surface (FIG. 4). As a result, labeled cells sediment onto the imaging surface of the deposition plate, but at most a few non-specific contaminating cells such as white blood cells (WBCs) ever reached the same level.

After sedimentation, the blood layer and the dense medium are aspirated, which removes the majority of contaminating cells. The next step is to wash, stain, and image cells on the same surface (FIG. 4, right). Cells such as EpCAM-expressing CTCs selected based on positive and negative fluorescent markers and morphology are subsequently recovered by automated micromanipulation to a deposition plate (e.g., a PCR plate or microtiter plate or strip of PCR tubes) for subsequent analysis (such as whole-genome amplification, library preparation, and sequencing). This format allows direct performance of cell enrichment on deposition plates using the macrowells to partition the samples.

Multi-Spectral Image Cytometry

Multi-Spectral Image Cytometry (MuSIC) uses an epi fluorescence microscope to access 16 phenotypic parameters simultaneously on 1,000 or 10,000 or 100,000 or 1,000,000 single cells. Substantially all cells remain viable and individually accessible for downstream analyses (e.g., biochemical analysis, metabolites, transcriptional profiling, targeted sequencing, single-cell RNA sequencing, whole exome sequencing, epigenetic measurements (e.g, methylation, histones, chromatin), whole genome sequencing, or clonal expansion).

The increased throughput of the new design enables more efficient processing of a greater number of samples, allowing scale-up of single-cell analyses not possible with previous designs. SBS format is used for automated high-throughput screening assays in the industry; the systems and methods presented herein have now employed the SBS format to phenotypic analyses at the single-cell level that preserve viability, identity, and potential for recovery of cells throughout an experiment. By compartmentalizing cells in the nanowells (a unique feature of assays presented herein), it is possible to improve isolation and simplify localization and recovery of individual cells of interest.

In certain embodiments, a multichannel beamsplitter is used to image the same block of wells (illuminated with a single excitation source) in multiple emission bands simultaneously using a single detector (e.g., with sufficiently large sensor area to accommodate multiple channels) to speed up total imaging time and reduce exposure of sensitive fluorophores to the corresponding excitation.

Exemplary fluorophores that can be used include, but are not limited to, the following: Calcein Violet, Alexa Fluor 488, BV605, PE, Alexa Fluor 568, BV650, PerCP, PE-Cys, Alexa Fluor 647, BV711, PerCP-eFluor710, PE-Alexa Fluor 700, BV786, PE-Cy7, APC-Cy7, and brilliant violet dye (e.g., BV711, BV786, BUV395, BUV496, BUV661, BUV737, BUV805, BB515, BV421, BV510, BV605, BV650, BV711, BV786), 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); AFPs—AutoFluorescent Protein—(Quantum Biotechnologies) see sgGFP, sgBFP; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); bis-BTC; Blancophor FFG; Blancophor SV; BOBO™-1; BOBO™-3; Bodipy 492/515; Bodipy 493/503; Bodipy 500/510; Bodipy 505/515; Bodipy 530/10; Bodipy 542/563; Bodipy 18/568; Bodipy 564/517; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson™; Calcium Green; Calcium Green-1 Ca.sup.2+ Dye; Calcium Green-2 Ca.sup.2+; Calcium Green-5N Ca.sup.2+; Calcium Green-C18 Ca.sup.2+; Calcium Orange; Calcofluor White; Carboxy-X-rhodamine (5-ROX); Cascade Blue™; Cascade Yellow; Catecholamine; CCF2 (GeneBlazer); CFDA; CFP—Cyan Fluorescent Protein; CFP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3' DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DiIC18(5)); DIDS; Dihydrorhodamine 123 (DHR); Dil (Di1C18(3)); Dinitrophenol; DiO (DiOC18(3)); DiR; DiR (DiIC18(7)); DM-NERF (high pH); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer (CCF2); GFP (S65T); GFP red shifted (rsGFP); GFP wild type, non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1, low calcium; Indodicarbocyanine (DiD); Indotricarbocyanine (DiR); Intrawhite Cf; JC-1; JO-JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant lavin EBG; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodaminelso ThioCyanate; True Blue; TruRed; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO-3; YOYO-1; YOYO-3, Sybr Green, Thiazole orange (interchelating dyes), semiconductor nanoparticles such as quantum dots, or caged fluorophore (which can be activated with light or other electromagnetic energy source) and/or combinations thereof.

In certain embodiments, several detectors simultaneously capturing each field of view (in different channels) can further decrease total imaging time and exposure. In certain embodiments, the use of a fast and sensitive detector (e.g., sCMOS) with a high pixel-count (e.g., 2048×2048) and a large (e.g., close to ¾" diagonal) sensor area in combination with a suitably low magnification (e.g., 4×/0.2NA) further facilitates simultaneous high-content and high-throughput imaging. In some embodiments, several imagers act in parallel on separate macrowells to speed up imaging time. In various embodiments, post-processing accounts for shading in nonhomogenous illumination profiles, either in software or hardware. In certain embodiments, microengraving captures elements of the secretome of each cell (in addition to phenotypic traits from cytometry), which greatly expands the amount of information and types of assays available for each cell.

Although exemplary embodiment analyses have been demonstrated to be suitable for CTCs and lymphocytes from mucosal samples, in certain embodiments the approach is applied to any area where identification and recovery of rare cells, or characterization of cellular heterogeneity, are needed, while only small numbers of cells may be available; it could equally apply to stem cells, bacteria and yeast, or highly heterogeneous tumors. In some embodiments, the current disclosure enables simultaneous high-content and high-throughput phenotypic characterization of single cells, while preserving cell viability and identity for further analyses. The format also allows perturbations of the cells by the addition of drugs, immunomodulators, antagonists, viruses, and the like. Along with standardization of the form-factor, this makes our approach modular enough to be integrated with existing analytical pipelines (e.g., ones comprising liquid handlers, automated incubators, sequencers, and the like) to enable an even greater degree of characterization of cells and ultimately improve understanding of biological processes and assist diagnostics.

Identification and Collection

Figure 5:
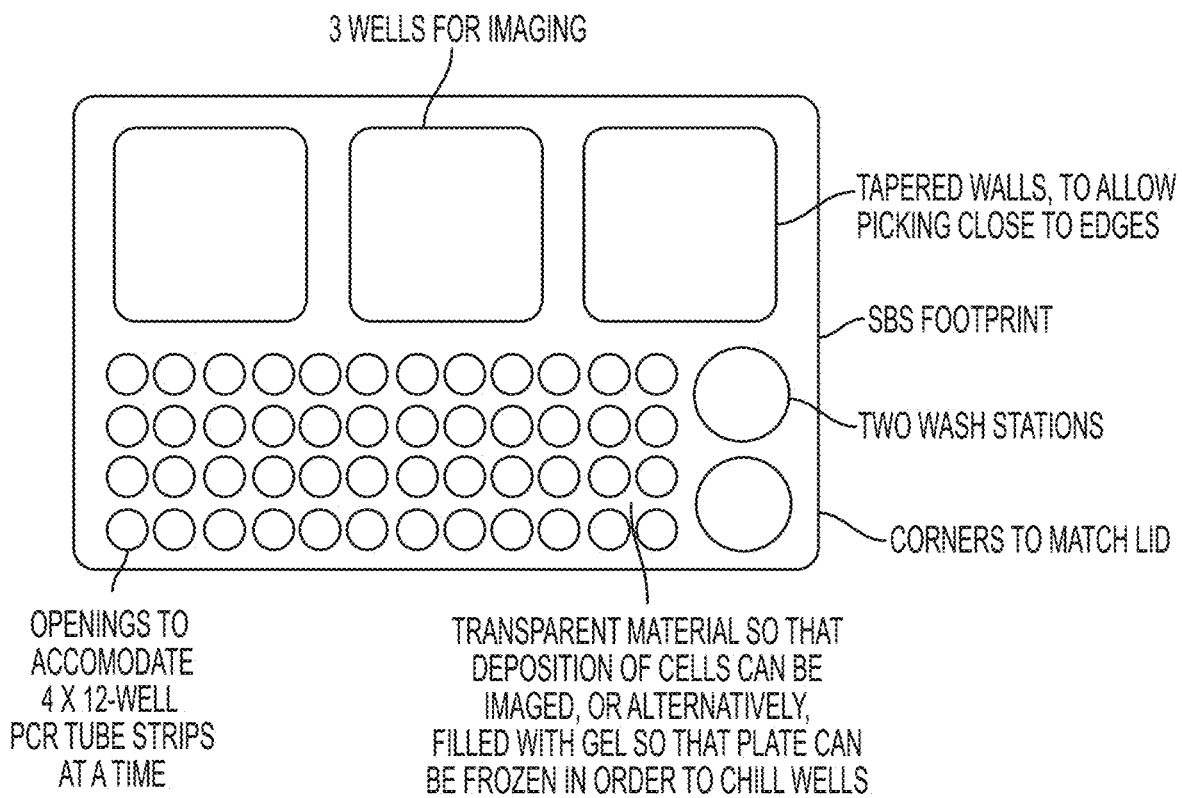
FIG. 5 shows a deposition well-plate that is manufactured such that sample wells and recovery wells are positioned closely. This well-plate solves the problem of distant movements among all of these stations (nanowells, receiving wells, wash wells). Existing solutions (e.g., CellCelector, micromanipulators) have separate stations that require distant travel from one location to the other.
Figure 6:
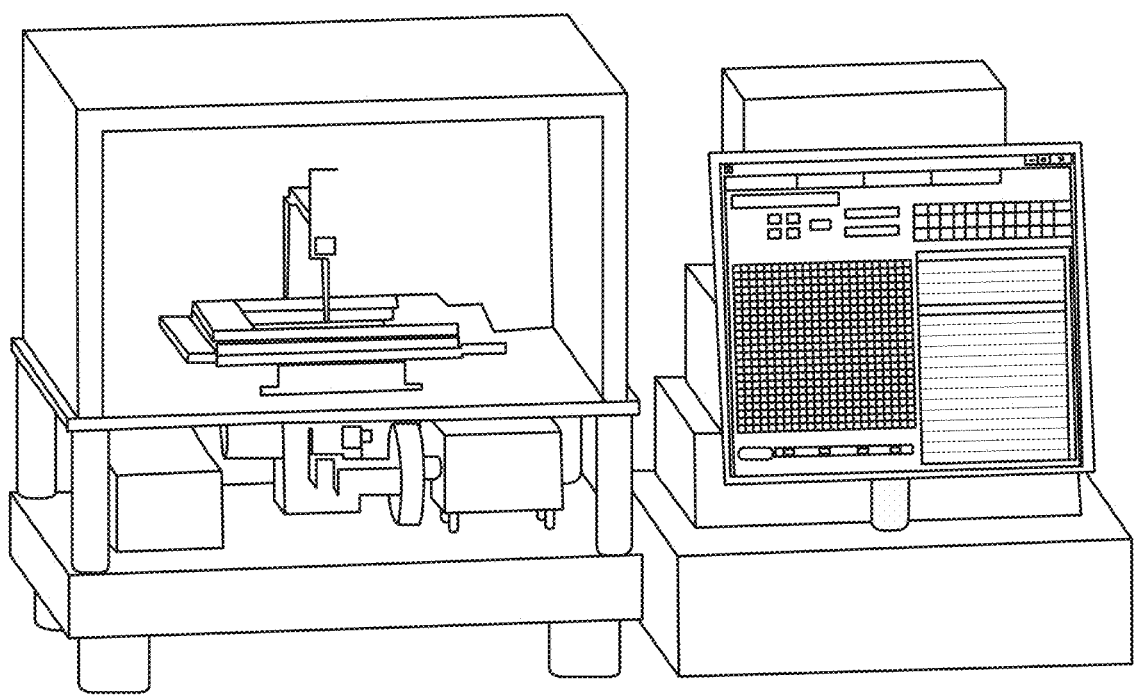
FIG. 6 shows an exemplary embodiment in which a deposition well-plate can be analyzed.

In the exemplary embodiments of FIG. 6, a deposition well-plate (FIG. 5) is manufactured such that sample wells and recovery wells are positioned closely. The close positioning enables an embodiment of the present disclosure to identify individual cells of interest in a sample well using a microscope and a processor, then selectively activate a set of actuators to manipulate a focus drive and a motorized stage upon which a deposition well plate is set. This well-plate solves the problem of distant movements among all of these stations (nanowells, receiving wells, wash wells). Existing solutions (e.g., CellCelector, micromanipulators) have separate stations that require distant travel from one location to the other. The well-plate shown in FIG. 5 further comprises two wash stations, three sampling wells for imaging, the wells having tapered walls to allow for picking close to their edges, an SBS footprint, and covers to match the lid. The well-plate shown in FIG. 5 has openings to accommodate 4×12-well PCR tube strips at a time. The well-plate is made of transparent material so that deposition of cells can be imaged, or alternatively, filled with gel so that the plate can be frozen in order to chill the wells.

After imaging of the sample wells, the captured images are analyzed and the locations of individual cells of interest are automatically detected. In certain embodiments, the cell locations are confirmed by an operator. The motorized stage and a focus drive are then automatically translated such that a micromanipulator arm with attached capillary needle is oriented above a particular cell of interest. A vertical actuator corresponding to constrained movement in the z-direction of the micromanipulator arm is translated downward into the recovery well at or sufficiently near the individual cell of interest. A small quantity of fluid containing the individual cell of interest is drawn by an actuated micropump into the capillary needle. Subsequently, the micromanipulator arm is raised out of the sample well and the motorized stage and the micromanipulator arm are automatically translated such that a recovery well is oriented beneath the micromanipulator arm. The capillary needle then dispenses the fluid containing the individual cell of interest into the recovery well.

Computing Environment

Figure 7:
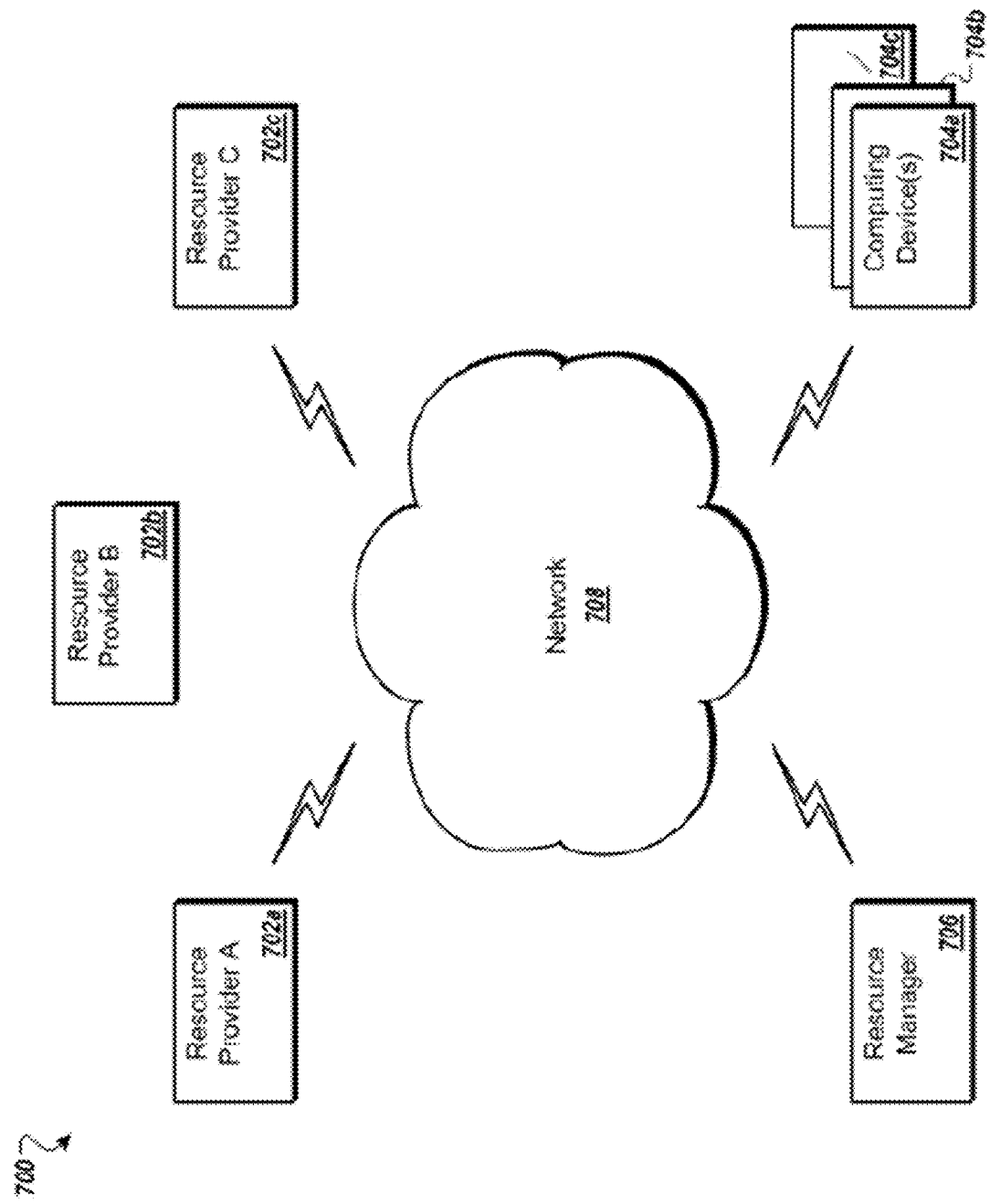
FIG. 7 is a block diagram of an example network environment for use in the methods and systems for analysis of spectrometry data, according to an illustrative embodiment.

FIG. 7 shows an illustrative network environment 700 for use in the methods and systems for analysis of cytometry data corresponding to particles of a sample, as described herein. In brief overview, referring now to FIG. 7, a block diagram of an exemplary cloud computing environment 700 is shown and described. The cloud computing environment 700 may include one or more resource providers 702a, 702b, 702c (collectively, 702). Each resource provider 702 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 702 may be connected to any other resource provider 702 in the cloud computing environment 700. In some implementations, the resource providers 702 may be connected over a computer network 708. Each resource provider 702 may be connected to one or more computing device 704a, 704b, 704c (collectively, 704), over the computer network 708.

The cloud computing environment 700 may include a resource manager 706. The resource manager 706 may be connected to the resource providers 702 and the computing devices 704 over the computer network 708. In some implementations, the resource manager 706 may facilitate the provision of computing resources by one or more resource providers 702 to one or more computing devices 704. The resource manager 706 may receive a request for a computing resource from a particular computing device 704. The resource manager 706 may identify one or more resource providers 702 capable of providing the computing resource requested by the computing device 704. The resource manager 706 may select a resource provider 702 to provide the computing resource. The resource manager 706 may facilitate a connection between the resource provider 702 and a particular computing device 704. In some implementations, the resource manager 706 may establish a connection between a particular resource provider 702 and a particular computing device 704. In some implementations, the resource manager 706 may redirect a particular computing device 704 to a particular resource provider 702 with the requested computing resource.

Figure 8:
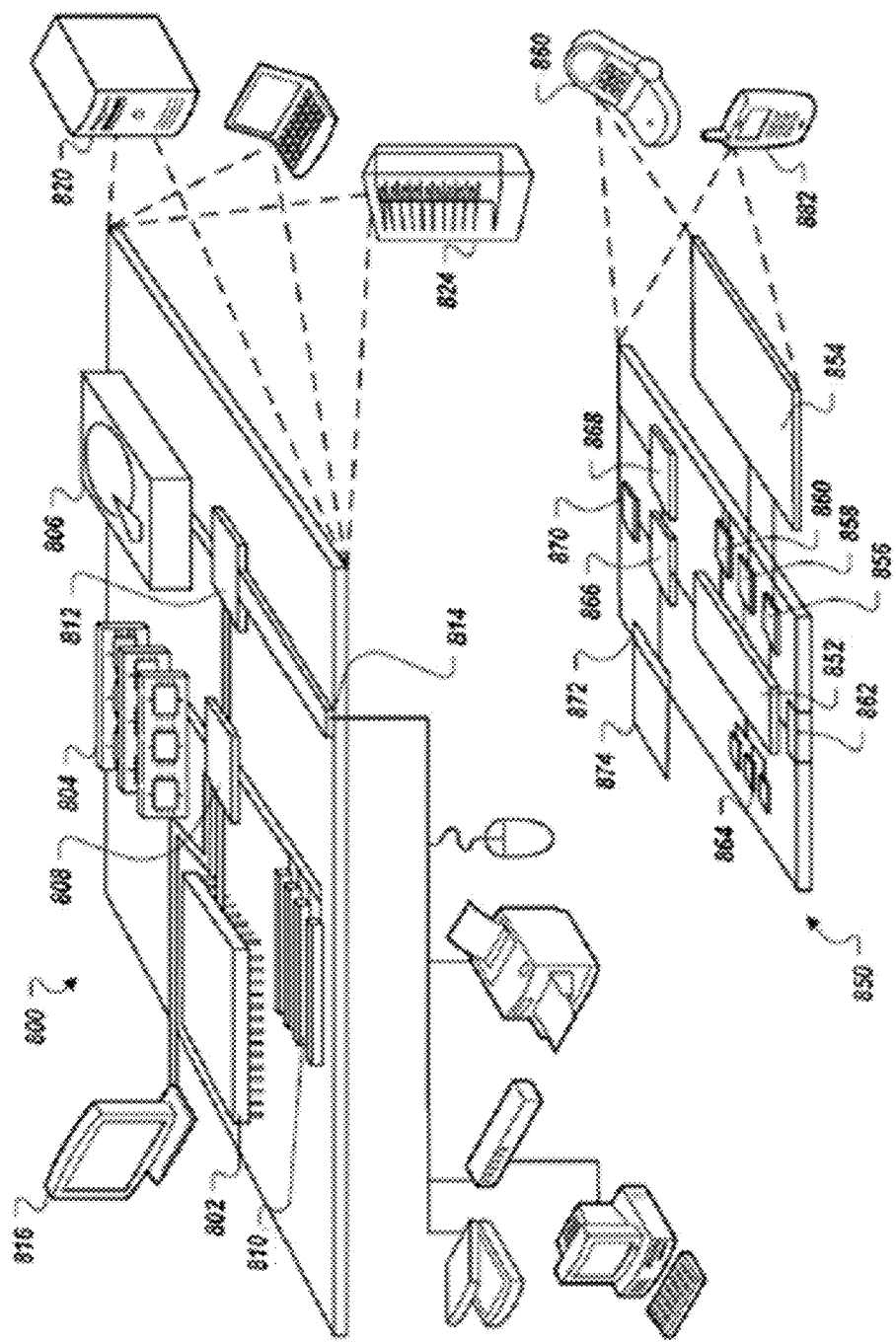
FIG. 8 is a block diagram of an example computing device and an example mobile computing device, for use in illustrative embodiments of the invention.

FIG. 8 shows an example of a computing device 800 and a mobile computing device 850 that can be used in the methods and systems described in this disclosure. The computing device 800 is intended to represent various forms of digital computers, such as laptops, desktops, workstations, personal digital assistants, servers, blade servers, mainframes, and other appropriate computers. The mobile computing device 850 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 800 includes a processor 802, a memory 804, a storage device 806, a high-speed interface 808 connecting to the memory 804 and multiple high-speed expansion ports 810, and a low-speed interface 812 connecting to a low-speed expansion port 814 and the storage device 806. Each of the processor 802, the memory 804, the storage device 806, the high-speed interface 808, the high-speed expansion ports 810, and the low-speed interface 812, are interconnected using various busses, and may be mounted on a common motherboard or in other manners as appropriate. The processor 802 can process instructions for execution within the computing device 800, including instructions stored in the memory 804 or on the storage device 806 to display graphical information for a GUI on an external input/output device, such as a display 816 coupled to the high-speed interface 808. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 804 stores information within the computing device 800. In some implementations, the memory 804 is a volatile memory unit or units. In some implementations, the memory 804 is a non-volatile memory unit or units. The memory 804 may also be another form of computer-readable medium, such as a magnetic or optical disk.

The storage device 806 is capable of providing mass storage for the computing device 800. In some implementations, the storage device 806 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 802), perform one or more methods, such as those described above. The instructions can also be stored by one or more storage devices such as computer- or machine-readable mediums (for example, the memory 804, the storage device 806, or memory on the processor 802).

The high-speed interface 808 manages bandwidth-intensive operations for the computing device 800, while the low-speed interface 812 manages lower bandwidth-intensive operations. Such allocation of functions is an example only. In some implementations, the high-speed interface 808 is coupled to the memory 804, the display 816 (e.g., through a graphics processor or accelerator), and to the high-speed expansion ports 810, which may accept various expansion cards (not shown). In the implementation, the low-speed interface 812 is coupled to the storage device 806 and the low-speed expansion port 814. The low-speed expansion port 814, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 800 may be implemented in a number of different forms, as shown in the figure. For example, it may be implemented as a standard server 820, or multiple times in a group of such servers. In addition, it may be implemented in a personal computer such as a laptop computer 822. It may also be implemented as part of a rack server system 824. Alternatively, components from the computing device 800 may be combined with other components in a mobile device (not shown), such as a mobile computing device 850. Each of such devices may contain one or more of the computing device 800 and the mobile computing device 850, and an entire system may be made up of multiple computing devices communicating with each other.

The mobile computing device 850 includes a processor 852, a memory 864, an input/output device such as a display 854, a communication interface 866, and a transceiver 868, among other components. The mobile computing device 850 may also be provided with a storage device, such as a micro-drive or other device, to provide additional storage. Each of the processor 852, the memory 864, the display 854, the communication interface 866, and the transceiver 868, are interconnected using various buses, and several of the components may be mounted on a common motherboard or in other manners as appropriate.

The processor 852 can execute instructions within the mobile computing device 850, including instructions stored in the memory 864. The processor 852 may be implemented as a chipset of chips that include separate and multiple analog and digital processors. The processor 852 may provide, for example, for coordination of the other components of the mobile computing device 850, such as control of user interfaces, applications run by the mobile computing device 850, and wireless communication by the mobile computing device 850.

The processor 852 may communicate with a user through a control interface 858 and a display interface 856 coupled to the display 854. The display 854 may be, for example, a TFT (Thin-Film-Transistor Liquid Crystal Display) display or an OLED (Organic Light Emitting Diode) display, or other appropriate display technology. The display interface 856 may comprise appropriate circuitry for driving the display 854 to present graphical and other information to a user. The control interface 858 may receive commands from a user and convert them for submission to the processor 852. In addition, an external interface 862 may provide communication with the processor 852, so as to enable near area communication of the mobile computing device 850 with other devices. The external interface 862 may provide, for example, for wired communication in some implementations, or for wireless communication in other implementations, and multiple interfaces may also be used.

The memory 864 stores information within the mobile computing device 850. The memory 864 can be implemented as one or more of a computer-readable medium or media, a volatile memory unit or units, or a non-volatile memory unit or units. An expansion memory 874 may also be provided and connected to the mobile computing device 850 through an expansion interface 872, which may include, for example, a SIMM (Single In Line Memory Module) card interface. The expansion memory 874 may provide extra storage space for the mobile computing device 850, or may also store applications or other information for the mobile computing device 850. Specifically, the expansion memory 874 may include instructions to carry out or supplement the processes described above, and may include secure information also. Thus, for example, the expansion memory 874 may be provided as a security module for the mobile computing device 850, and may be programmed with instructions that permit secure use of the mobile computing device 850. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 852), perform one or more methods, such as those described above. The instructions can also be stored by one or more storage devices, such as one or more computer- or machine-readable mediums (for example, the memory 864, the expansion memory 874, or memory on the processor 852). In some implementations, the instructions can be received in a propagated signal, for example, over the transceiver 868 or the external interface 862.

The mobile computing device 850 may communicate wirelessly through the communication interface 866, which may include digital signal processing circuitry where necessary. The communication interface 866 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 868 using a radio-frequency. In addition, short-range communication may occur, such as using a Bluetooth®, Wi-Fi™, or other such transceiver (not shown). In addition, a GPS (Global Positioning System) receiver module 870 may provide additional navigation- and location-related wireless data to the mobile computing device 850, which may be used as appropriate by applications running on the mobile computing device 850.

The mobile computing device 850 may also communicate audibly using an audio codec 860, which may receive spoken information from a user and convert it to usable digital information. The audio codec 860 may likewise generate audible sound for a user, such as through a speaker, e.g., in a handset of the mobile computing device 850. Such sound may include sound from voice telephone calls, may include recorded sound (e.g., voice messages, music files, etc.) and may also include sound generated by applications operating on the mobile computing device 850.

The mobile computing device 850 may be implemented in a number of different forms, as shown in the figure. For example, it may be implemented as a cellular telephone 880. It may also be implemented as part of a smart-phone 882, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Nanobox for Performing High Quality Multicolor Slide Cytometry

In certain embodiments, the processor includes a fully integrated module ("Nanobox") for performing high quality multicolor slide cytometry. Nanobox has several components that automate image calibration, nanowell grid identification, cell identification, data extraction, spectral spillover compensation, and in silico F-minus one generation for automatic calling of positive signal. This process traditionally requires measuring an independent sample to collect F-minus one data for compensation, which can be accomplished with beads stained with all fluorophores used (minus one) in different combinations. This is a tedious process. The best results are achieved when these samples use cells instead of beads since they are more similar to the cells tested. The limitation is that the cells can be extremely limited in number from tissue. The in silico process described herein solves this problem by enabling compensation directly from the tested cells (no calibration sample required).

Figure 9A:
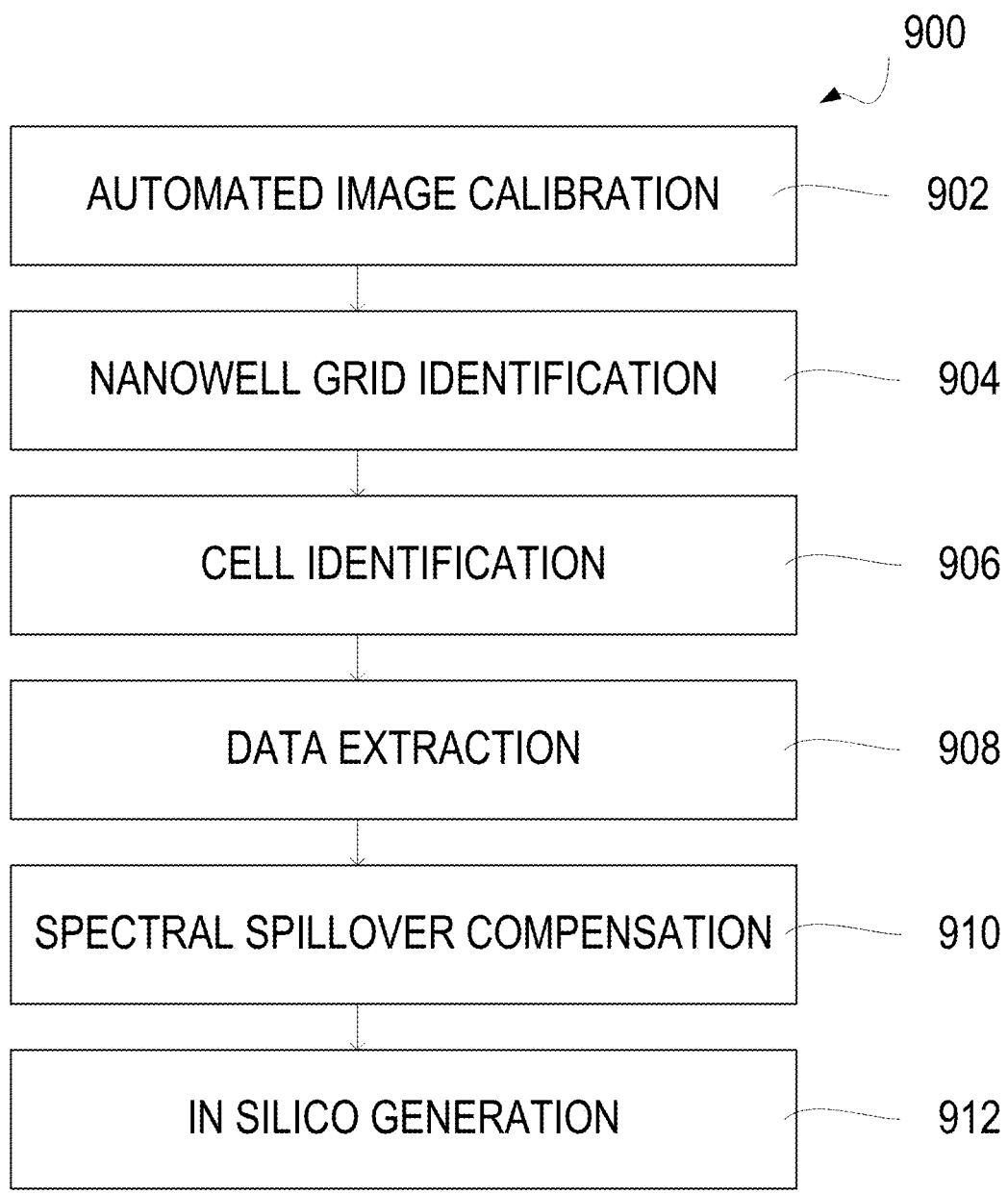
FIG. 9A is a flow chart 900 depicting steps performed by an exemplary nanobox module, according to an illustrative embodiment. As the term is used herein, "nanobox" refers to a module (e.g., set of instructions) for execution by a processor of a computing device, in particular, in certain embodiments, a cytometry module for performing a cytometry procedure. Step 902 is automated image calibration, step 904 is nanowell grid identification, step 906 is cell identification, step 908 is data extraction, step 910 is spectral spillover compensation, and step 912 is in silico F-minus one generation.
Figure 9B:
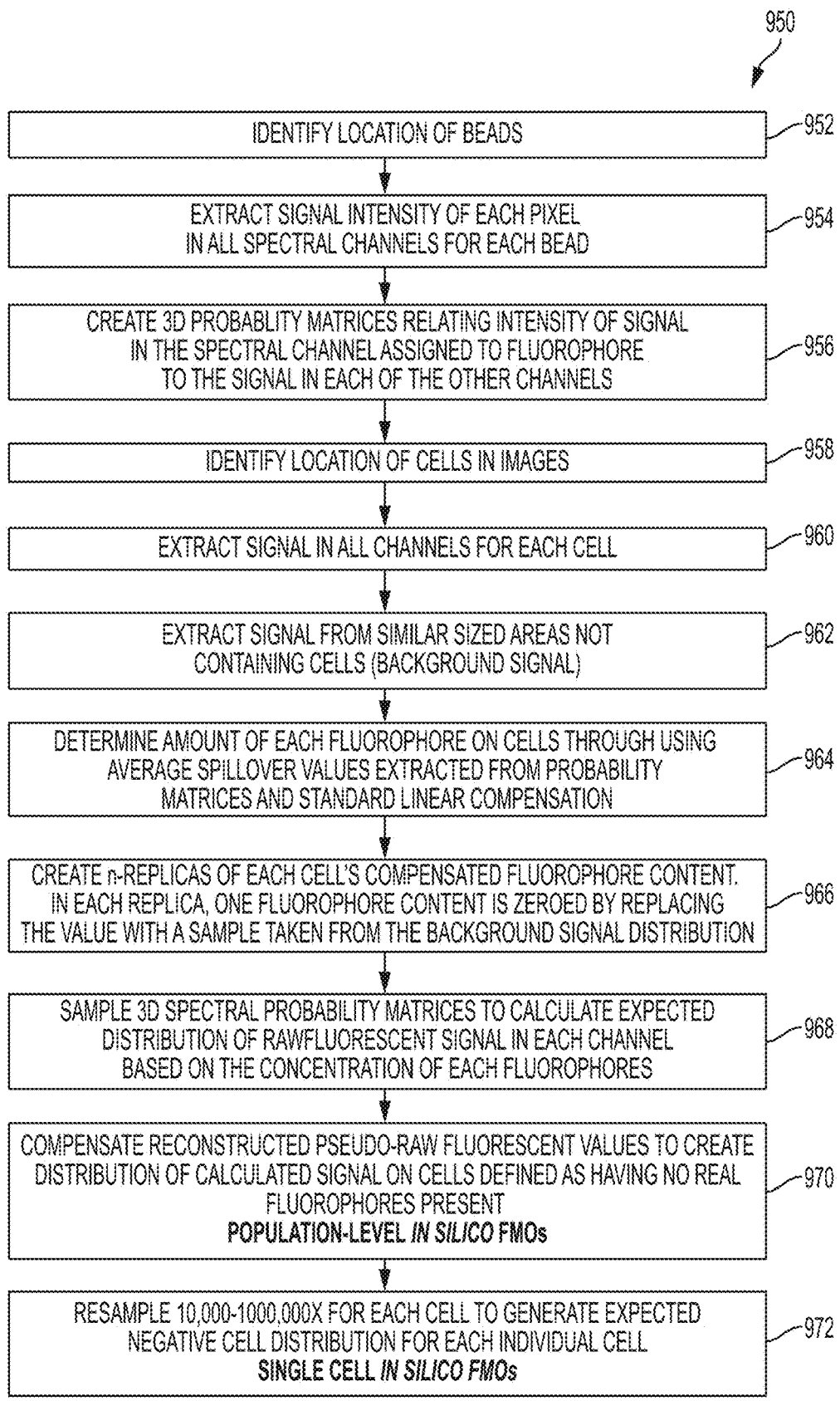
FIG. 9B depicts further detail involved in the in silico F-minus one generation step 912.

In certain embodiments, all steps can be accomplished with about 5 minutes or less of hands-on user input and use a parallel processing framework for rapid, distributed data analysis. The module can be used both in stand-alone mode (e.g., for processing a set of specimen images acquired previously), and real-time mode (e.g., for processing specimen images as they are being acquired). FIG. 9A is a flow chart 900 depicting steps performed by an exemplary nanobox module, according to an illustrative embodiment. Step 902 is automated image calibration, step 904 is nanowell grid identification, step 906 is cell identification, step 908 is data extraction, step 910 is spectral spillover compensation, and step 912 is in silico F-minus one generation. FIG. 9B depicts further detail involved in the insilico F-minus one generation step 912.

Image Calibration (Reference 902)

Nanobox automatically extracts from the metadata of the image files the identity of the microscope used to acquire the data, the date the data was acquired, and all relevant information about the spectral channels used in the experiment (or in real-time mode, obtains relevant information directly from other modules). The metadata is used to automatically select from a library of calibration frames, the appropriate dark, flat field, and illumination calibration frames for each spectral image for that microscope on the date the data was collected. The calibration library is populated by running defined calibration programs on the microscope monthly. The final calibrated image is created through the equation:

$$I_c = ((I_r - DF)./FF)./IF$$

where: $I_c$=Calibrated image, $I_r$=raw image, DF=dark frame, FF=flat field frame, IF=illumination frame and ./ denotes element-wise division.

Dark Frame—Dark calibration frames are created by collecting a series of images with no excitation light using a combinatorial combination of exposure times and camera gain settings in the typical range for cytometry. All images acquired with the same combination of exposure time and gain are averaged to create the dark frame for those settings. Nanobox selects the dark frame with the closest combination of exposure time and gain used for each spectral channel.

Flat Field Frame—The flat field calibration frames are created by collecting a series of images of unstructured transmitted light passing through the dichroic and each emission filter. The images for each filter are averaged. The dark calibration frame acquired with the same exposure and gain settings is subtracted from the flat field image and then the image is normalized by the mean pixel intensity of all pixels in the image to acquire the flat field calibration frame for each emission filter. Nanobox selects the correct flat field frame to apply by determining the emission filter used for each spectral channel in the dataset.

Illumination Field Frame Illumination calibration frames are created by acquiring series of images of a set of uniformly fluorescent slides using each excitation channel. Images within each image series that contain unique anomalies in the fluorescent field are automatically discarded. The remaining images are averaged. The appropriate dark frame is subtracted from the averaged image followed by division by the appropriate flat field frame. Finally, the image is normalized by the mean pixel intensity to acquire the illumination calibration frame for each excitation channel.

Nanobox selects the correct illumination field frame to apply by determining the excitation light used for each spectral channel in the dataset.

Alternatively to constructing a library of images for each set of microscope settings, dark frame calibration may be performed at the start of each acquisition of specimen data. This procedure provides protection against extraneous changes (e.g., due to shifts in the optical train caused by vibration or accidentally by a user) happening between runs, and increases accuracy of the method. Flat field and illumination field frames are then adjusted accordingly.

Nanowell Grid Identification (Reference 904)

Nanobox employs a fully-automated algorithm to identify the location of nanowells in the spectral image series of each array location. The algorithm initially uses a Radon transformation of the transmitted light image to identify the rotation of the nanowell grid in the image. The transmitted light image is then rotated the calculated amount. 1-D projections of the rotated image onto the x- and y-axes are analyzed for the expected frequency of well edges based on the well size and well spacing, identifying starting and stopping points coordinates for wells in the image. Often, nanowell arrays are designed where the inter-well spacing is equivalent to the well size (e.g., 50 µm wells with 50 µm spacing), making it impossible to determine from the 1D traces which signals represent the start or end of wells. This is determined by Nanobox by calculating similar 1D projections of a Sobel transformation of the rotated image, which turns the image into a binary image where only edges have a value of 1. Projections of the well areas will have higher values in these 1D traces than the inter-well spaces due to the presence of the edges parallel to projection axis. With this information, Nanobox defines the location of the x- and y-grid of the nanowells in the image. Finally, the algorithm uses simple trigonometry to transform the coordinates of each well to designate the same area in the original image.

Cell Identification and Data Extraction (References 906 and 908)

In certain embodiments, nanobox uses a segmentation thresholding algorithm for identifying weak signal above background that was designed to be agnostic to the number of cells present in the image. The algorithm applies a sliding threshold to each spectral channel designated by the user to be used to identify cell locations. For each threshold, the number of single pixel objects in the binary image defined by the threshold are calculated. Plotting the threshold value versus the number of single pixel objects creates an L shaped curve where the number of single pixel objects changes little as the threshold is decreased until an inflection point is reached where the number of single pixel events increases rapidly with decreases in threshold. A simple geometric analysis of this plot (e.g., finding the intersection of two chord lines) is used to determine the threshold at the inflection point, yielding the lowest threshold possible before a large amount of background signal would be called positive. By focusing on single pixel objects, the algorithm bases the threshold solely on the distribution of background pixels, because positive signals from cells rarely appear as single pixel events. This makes the algorithm far more robust to variances in the number of cells in the image compared to other auto-thresholding algorithms that use statistical measures to characterize total pixel distributions.

Additionally, Nanobox is able to further split the segmented areas comprising two or more adjacent cells (e.g., based on the inverted watershed method seeded by the local maxima in pixel intensities).

After segmentation, Nanobox applies various astronomical aperture photometry concepts in new ways to measure the intensity of fluorescent signal in each spectral channel. To maximize the signal to noise ratio (SNR) of the signal extracted from each cell, an aperture of 5-8 pixels is set within the defined cell area to minimize dilution of the signal from the decrease of signal near the periphery of the cell. The aperture for each cell is defined by rank ordering the intensity of the fluorescent signal in the spectral channel used to define the location of the cell and selecting the brightest 5-8 pixels. The signal for those pixels in all other spectral channels is then extracted and exported for further analysis. If multiple segmentation channels are used, Nanobox creates a unique "cell object" for each segmentation channel, and analyses it separately from the rest.

Spectral Spillover Compensation (Reference 910)

In order to quantitate the number of fluorescent molecules detected in a given spectral channel on a cell, spillover of signal from fluorophores in neighboring spectral channels into the current channel must be taken into account. During the initial setup, Nanobox loads images of beads stained singly with each fluorophore used to stain the cells. Nanobox automatically locates beads within the images (e.g., using the same segmentation algorithm as for cells) and extracts the average spillover spectral properties of each fluorophore. Using well established techniques from flow cytometry, Nanobox automatically uses this information to determine the true amount of each fluorophore present on each cell by multiplying the raw intensities extracted from each spectral channel by the inverse spillover matrix generated from the spillover beads. This data is exported as final compensated fluorophore counts for each cell.

In Silico FMO (FIG. 9A, Reference 912, and FIG. 9B)

Fluorescence-based cytometry is a widely used tool for the analysis of protein and more recently RNA expression of large number of single cells. Recent advances in optics and dye chemistry have enabled the simultaneous measurement of 10-30 different fluorescent molecules on each cell. However, this depth of data acquisition ensures significant spillover between the spectral channels due to the broad excitation and emission peaks of most fluorescent dyes. To calculate the amount of each fluorophore on a cell, the spillover signal in the fluorescent channel designated for the fluorophore is removed through an in silico process called compensation. Although required, compensation inevitably adds considerable error to the resulting measure, manifesting in a widening of the data distribution and often adding a skew to the distribution, the result of which makes it challenging to determine where a positive threshold should be set in a robust and reproducible manner.

It is possible to implement "F-minus one" (FMO) controls. in which separate portions of the same sample are stained with an antibody panel that contains all the antibodies but one. The distribution of the signal of the removed fluorophore is used to define the positive threshold for the missing dye as it is known that all cells are negative in the control. Although critical for accurate positive cell calling, FMOs are very burdensome to perform especially in high content cytometry because an FMO control is required for each channel. For staining a single sample of 100,000 cells with 12 antibodies for ~$18 in reagents, the FMOs require over a million cells and $190 in reagents and significantly more FTE time. When hundreds of samples are contemplated, FMOs become a serious drain of resources. Even more challenging, many types of clinical samples simply do not have enough cells to perform the controls, complicating analysis of these precious samples with this powerful technology.

Beyond cost and cell requirements, the classic FMO approach has another weakness in that it sets global thresholds based primarily on cells with the highest amounts of error (e.g., edges of the negative signal distribution) caused by the highest amounts of spillover signal from bright staining in another channel. This weakness is a result of using an average spillover value, making it impossible to create a predicted negative distribution without considering all the cells. This approach however has significant consequences for the sensitivity of detecting fluorescence on cells with little spillover, where the error will be much lower than cells with high levels of spillover. Segregation of the population into similar cells before applying FMOs is also a limited technique.

Nanobox also employs an algorithm for determining the probability that the compensated fluorescent signal for a given cell is higher than the background, taking into account the added error from spillover compensation. While extracting the basic spillover data from the singly-stained beads, Nanobox also builds n×(n−1) 3-dimensional probability distributions of the amount of signal measured in each spectral channel associated with a given amount of each fluorophore. Once Nanobox has determined the amount of each fluorophore on a given cell, it creates n "F-minus one" (FMO) replicas of the cell in which the value of one of the fluorophores is set to zero in each FMO. For population level analysis mode, the expected amount of measured signal in the channel measuring the fluorophore set to zero is determined by randomly sampling the 3D probability distributions of the other fluorophores' spillover signal into that channel using the calculated amount of each fluorophore on the cell. This signal is added to a random sampling of the background pixel signal distribution in the channel, creating the "pseudo-raw" FMO data. These values are then subjected to the same compensation calculation used on the real data, yielding the expected signal distribution of cells containing no fluorophores for the channel, given the population distribution of all the other fluorophores. This negative distribution can then be used to calculate the probability that the signal associated with any cell is significantly higher than the expected population background. This approach can also be performed on a per cell basis. In this approach, each cell is used to make 10,000 FMO replicates, each of which is used to create raw FMO values by randomly sampling the 3D spillover signal distributions. These FMOs are then used to create a unique negative signal distribution for each cell based on the amount of each fluorophore on that cell. This approach is useful when analyzing small numbers of cells where there are not enough cells to create population level FMOs. It also increases the sensitivity to low amounts of signal by considering only the amount of spillover error appropriate for the fluorophores present on each particular cell instead of the average amount of error for the population which is the standard in the field today.

Figure 10:
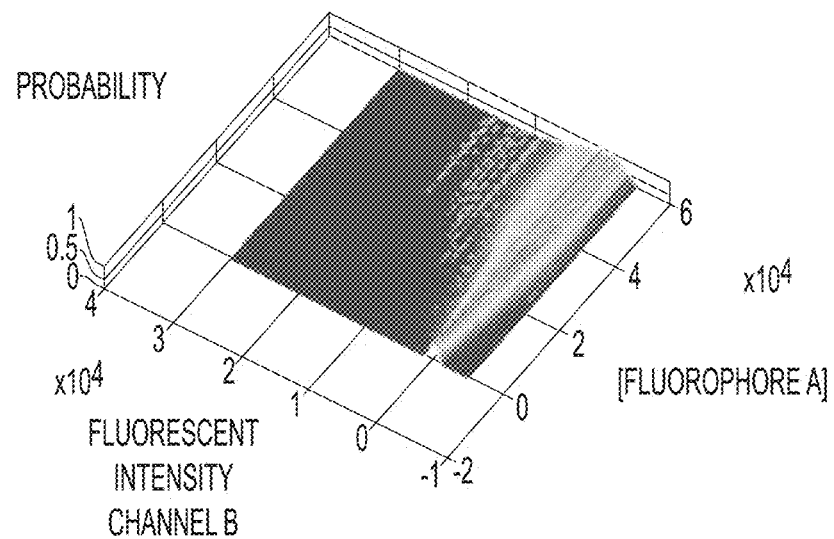
FIG. 10 shows 3D spectral probability matrices of fluorophores detected in channels. The x axis shows the amount of fluorophore. The y axis shows the amount of signal in incorrect spectral channel. The z axis shows the probability and spillover intensity.
Figure 10:
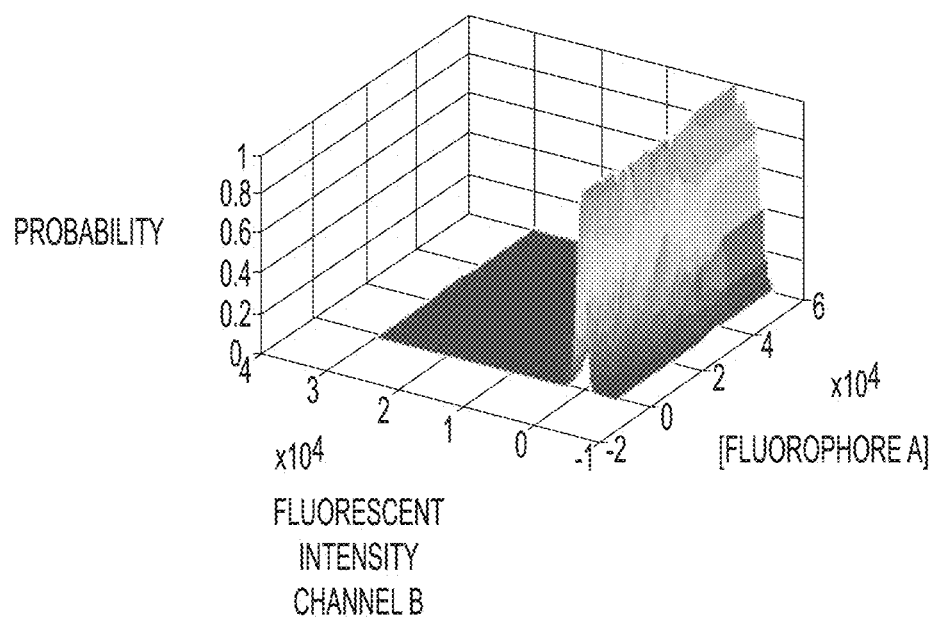

FIG. 9B shows an exemplary flow chart 950 for in silico FMO generation. Prior to execution of the in silico FMO generation procedure, certain data is acquired. In certain embodiments, acquired data includes: n-spectral images of compensation beads stained individually with each fluorescent molecule acquired with same microscope settings as cells and n-spectral images of cells stained with all fluorescent molecules. Step 952 is identification of the location of the beads, step 954 is extraction of signal intensity of each pixel in all spectral channels for each bead, step 956 is creation of a 3D probability matrices relating intensity of signal in the spectral channel assigned to fluorophore to the signal in each of the other channels (See FIG. 11 below for detail), step 958 is identification of the location of cells in images, step 960 is extraction of signal in all channels for each cell, step 962 is extraction of signal from similar sized areas not containing cells (background signal), step 964 is determination of amount of each fluorophore on cells through using average spillover values extracted from probability matrices and standard linear compensation, step 966 is creation of n-replicas of each cell's compensated fluorophore content (in each replica, one fluorophore content is zeroed by replacing the value with a sample taken from the background signal distribution), step 968 is generation of sample 3D spectral probability matrices to calculate expected distribution of raw fluorescent signal in each channel based on concentration of each fluorophores, step 970 is compensation of reconstructed pseudo-raw fluorescent values to create distribution of calculated signal on cells defined as having no real fluorophores present "Population-level in silico FMOs", and step 972 is resampling of 10,000-1000,000 times for each cell to generate expected negative cell distribution for each individual cell "Single cell in silico FMOs". FIG. 10 contains the probability that a given amount of fluorophore will emit a given amount of light detected in a second spectral channel. N−1 matrices are generated for each fluorophore.

Figure 11:
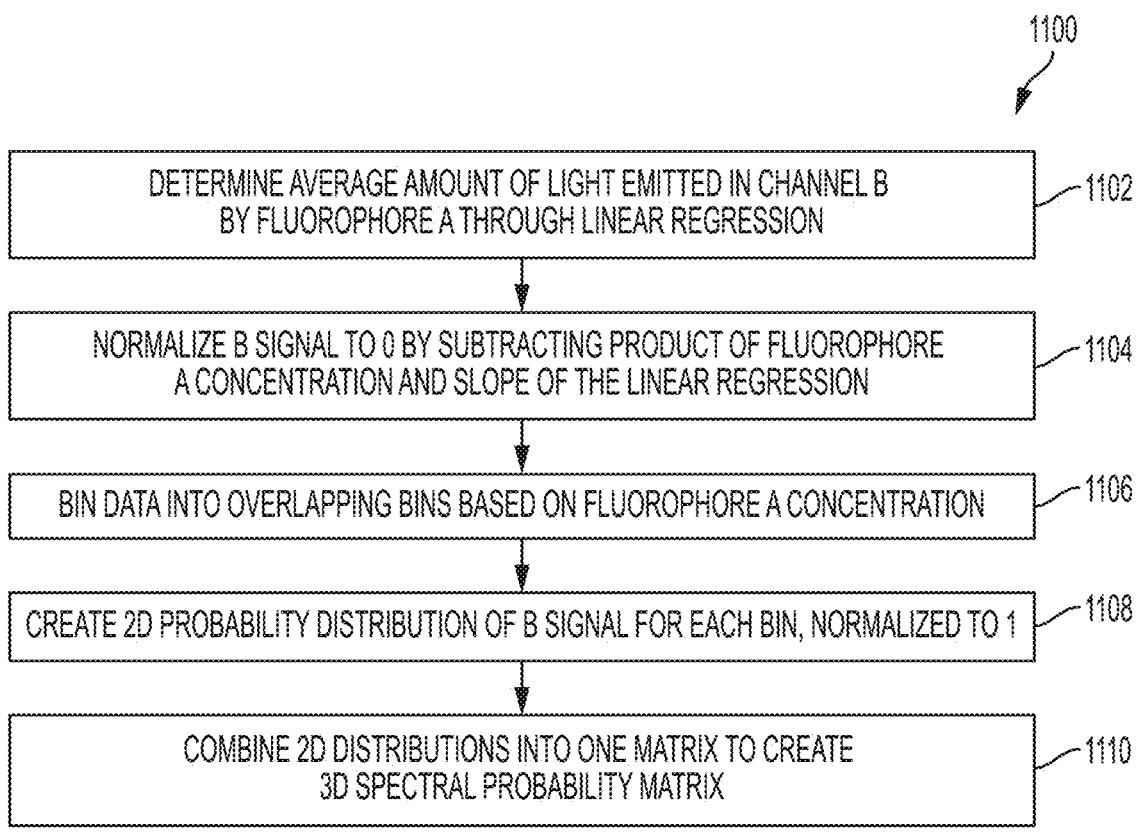
FIG. 11 shows a flow chart of generating 3D spectral probability matrices.

FIG. 11 shows a flow chart 1100 of generating 3D spectral probability matrices. The data is derived from spectral intensity of pixels extracted from images of beads labeled with single fluorophores. Generating a matrix relating to the signal in spectral channel B to amount of fluorophore A is performed via using data from beads labels with fluorophore A in accordance with the steps 1102-1110 provided in FIG. 11. Step 1102 is determination of average amount of light emitted in channel B by fluorophore A through linear regression, step 1104 is normalization of B signal to 0 by subtracting product of fluorophore A concentration and slope of the linear regression, step 1106 is binning of data into overlapping bins based on fluorophore A concentration, step 1108 is creation of 2D probability distribution of B signal for each bin, normalized to 1, and step 1110 is combination of 2D distributions into one matrix to create 3D spectral probability matrix.

In order to enable high content cytometry of small cell samples, an algorithm for generating FMO controls was generated in silico using the data already collected for the initial compensation of the spillover signal. The algorithm works by generating what a 3D spectral probability matrices from typical compensation bead data, as described above. Each spectral matrix contains the probability that a given amount of a fluorophore will produce any given amount of spillover signal in a different spectral channel. When expressed graphically, the x-axis is concentration of a fluorophore, the y-axis is signal in a particular spectral channel and the z axis is the probability that any two combinations will occur. A unique matrix is generated for each combination of fluorophore and spectral channel. To generate in silico FMOs, the compensated cell data is replicated n-times for an n-channel experiment. In each replicate dataset, the concentration of a different fluorophore is set to zero. The spectral matrices are then sampled to recreate a "pseudo-raw" intensity dataset which predicts the distribution of raw signal that would be predicted to occur in the channel if no actual fluorophore was present. The dataset is then recompensated to yield the signal distribution of the negative population. By sampling the probability distributions of spectral spillover instead of a single average value, errors added to the negative cell distribution including distribution skewing that is lost with the classical approach are able to be predicted. The predicted negative cell distribution can then be used to automatically set a positive threshold or give a p-value for the probability that any given cell has positive fluorescent signal, replicating the output of classic FMO controls. This is referred to as population level FMO generation.

In certain embodiments, the algorithm can create unique negative distributions for each cell in the dataset based on the specific concentration of fluorophores on each cell. The fluorophore content of each cell is used to iteratively sample the spectral matrices, creating a dataset of all the possible fluorescent signal intensities that would be observed given the amount of fluorophores on any cell, minus one. This data is then processed like the population level data to create negative signal distributions for each cell. This approach has two major advantages—increasing sensitivity to low amounts of signal on cells with little spillover and more robust FMO generation for samples with small numbers of cells. This is referred to as individual FMO generation.

The algorithm generates robust signal distributions of negative cells that takes into account all errors introduced into high content cytometric data during compensation. In certain embodiments, the algorithm is used to automatically call cells positive based on population level thresholds. In certain embodiments, the algorithm generates a predicted distribution for each individual cell, increasing sensitivity to low signal levels on cells with little spillover error. The algorithm can eliminate a major drain on resources in high content cytometric analysis as well as enable the use of the technology on small cell samples. The algorithm is applicable to either flow or slide based cytometry and likely has utility in other settings with high levels of multiplexing.

In certain embodiments, the algorithm enables robust automated calling of positive fluorescent signal in the context of significant crosstalk between fluorescent channels. In certain embodiments, the algorithm generates critical for high content cytometry, both flow cytometry and slide-based cytometry. In certain embodiments, the algorithm provides vast improvement over current approach in flow which use F-minus one controls—large saving in time, reagents and precious sample. In certain embodiments, the algorithm enables high content cytometry for small cell clinical samples that do not have enough cells to perform FMO controls.

EXAMPLE

The present example provides improvements compared to current flow systems. These improvements are particularly useful, although not limited, in the field of immunohistochemistry of tissue sections and highly multiplexed microarrays, where imaging of samples with limited lifespan and analyzing results in real-time is critical.

The features described below improved the image quality compared to conventional systems. For example, most single sensor image spectrometers achieve separation of each subimage by having each beam hit the lens at different angles. However, this can cause significant image aberrations which are significantly amplified in wide field settings. To overcome this, each beam is instead focused on a mirror array facing the final imaging lens. The angles of the mirrors in the array reflect the each beam directly toward the final lens, essentially recreating a new image on the mirror array that has each beam focused in a separate section.

The approach described herein focuses on each spectral channel. To correct the longitudinal chromatic aberration caused by filtering a converging beam and the other optical components, the individual reflecting mirrors that aim each beam at the central mirror array can be independently adjustable along the primary optical axis, enabling shortening or lengthening the focal point of each spectral color independently, allowing perfect correction of longitudinal chromatic aberration, critical for cytometric analysis of pinpoints of light.

Figure 13:
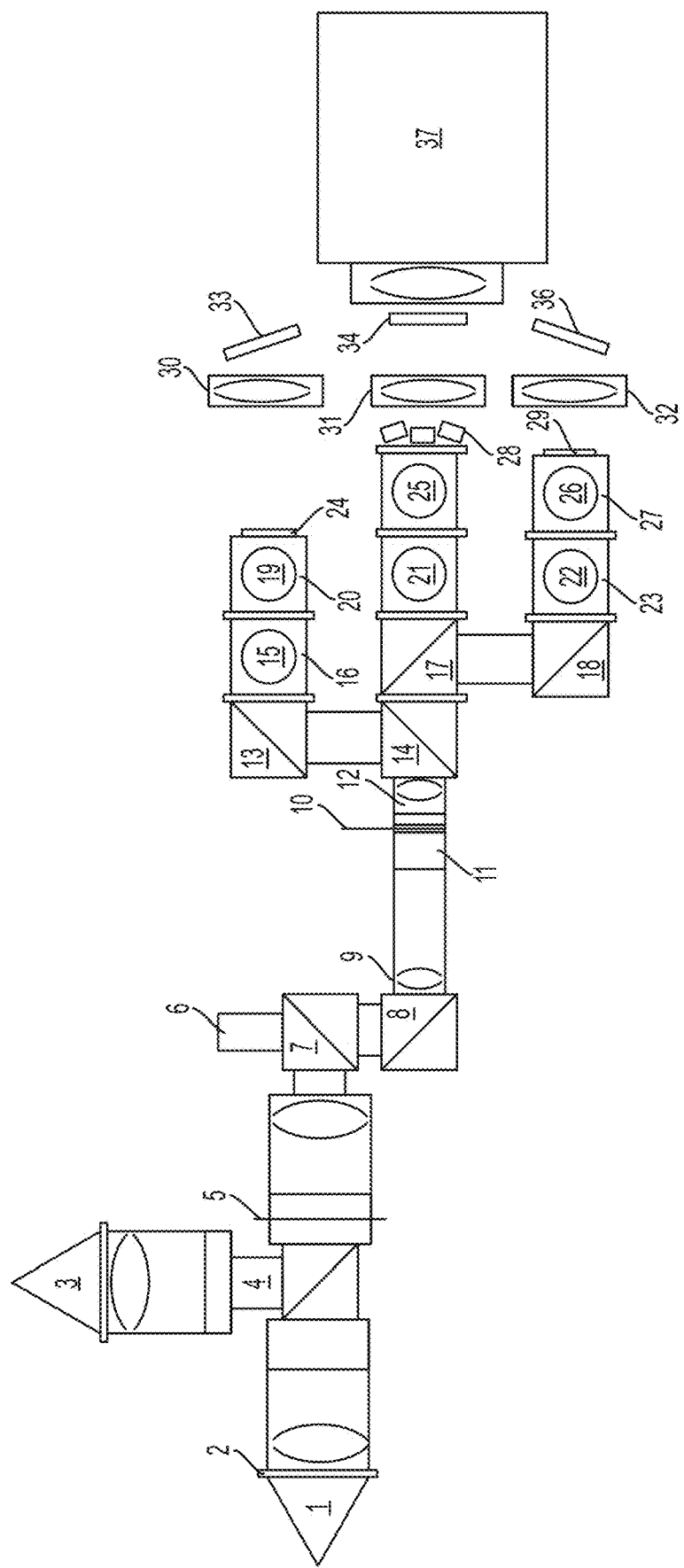
FIG. 13 shows a schematic of a microscope design as described herein.

Data Points on Imaging Speed:

The described improvements below provided an imaging speed of 55 mm$^2$/min in 12 fluorophores or channels, which can be extrapolated to 45 cm$^2$/min for 16 fluorophores or channels of data. In certain embodiments, the speed reaches 300 mm$^2$/min for imaging both 12 and 16 fluorophores or channels and includes 8 channels using a microscope. FIG. 13 shows a CAD drawing of a microscope that would perform imaging speeds at about 300 mm$^2$/min.

Referring to FIG. 13, (1) is a LLG collimator, (2) is a field stop iris, (3) is a UV LED collimator, (4) is a UV dichroic, (5) is 1650 μm$^2$ Square slit field stop iris, (6) is an Objective, (7) is a Quad dichroic, (8) is a Turning mirror, (9) is a Focal lens, (10) is an Image plane, (11) is a 1650 μm$^2$ Slit, (12) is a Converging lens, (13) is a Mirror, (14) is a Band 1-3 dichroic, (15) is a Band 1 dichroic—back, (16) is a Right turning mirror and Band 1 filter behind, (17) is a Band 4-5 dichroic, (18) is a Mirror, (19) is a Band 2 dichroic—forward, (20) is a Right turning mirror and Band 2 filter in front, (21) is a Band 7 Dichroic Back (behind 7 filter), (22) is a Band 4 dichroic—back, (23) is a Right turning mirror and Band 4 filter behind, (24) is a Band 3 filter, (25) is a Turning mirror forward (band 8 filter), (26) is a Band 2 dichroic—forward, (27) is a Right turning mirror and Band 5 filter in front, (28) is an Image mirror array, (29) is a Band 6 filter, (30) are 3 relay lens (front, plane, back), (31) are 2 relay lens (front, back), (32) are 3 relay lens (front, plane, back), (34) is a Final focal lens, (35) are 2 focusing mirrors in front and behind, (36) are 3 focusing mirrors, and (37) is a CMOS.

Comparators:

Commercial Zeiss microscope designed for similar imaging provides imaging speeds of about 7 mm$^2$/min for 16 fluorophores or channels.

High-end Genepix slide scanners with the same resolution as the system described herein is approximately 100 mm$^2$/min for 1 fluorophore or channel, which can be extrapolated to 8 mm$^2$/min for 12 fluorophores or channels. Calculations of imaging speeds are shown in Table 1.

In Table 1, the Present system, as described herein, estimates for 12 channels on the present system (not including the improvements described below with respect to FIG. 13) are based on an imaging run that produced the data in FIGS. 14A and 14B, discussed in more detail below. The 16 channel times were extrapolated based on time/channel of the 12 channel run. The Further updated system is a constructive embodiment, as depicted and described in more detail below with respect to FIG. 13, where time estimates were calculated theoretically based on the time required to image the same number of channels on the Present system. The slide scanner (Genepix 4400—Molecular Devices) timing is derived from time stamps of 4 channel scans of similarly sized glass slides at the same spatial resolution. Scanning time is directly scalable to channels as it performs the same process for each channel. The commercial scope (Zeiss AxioObserverZ1) times are based on an average of imaging runs performed.

TABLE 1

| System | Field of view, mm | Number of columns | Number of rows | Number of channels | Time per position, ms | Total area, mm$^2$ | Total time, min | Speed, mm$^2$/min |
|---|---|---|---|---|---|---|---|---|
| Commercial microscope | 0.8 | 24 | 72 | 16 | | 1105.9 | 150 | 7 |
| Commercial slide scanner | | | | 12 | | 1518 | 180 | 8 |
| Present system, hardware-triggered | 1.25 | 15 | 46 | 16 | 2135 | 1078.1 | 24.6 | 44 |
| Present system, hardware-triggered | 1.25 | 15 | 46 | 12 | 1735 | 1078.1 | 20 | 54 |
| Further updated system, hardware-triggered (all data estimated) | 1.65 | 11 | 35 | 23 | 650 | 1048.2 | 4.2 | 250 |
| Time to move the stage, ms | | 150 | | | | | | |
| Time to switch the filter wheel position, ms | | 55 | | | | | | |
| Number of filter wheel positions | | 8 | | | | | | |
| Average exposure time, ms | | 100 | | | | | | |
| Number of light sources | | 5 | | | | | | |

Improvements to System:

An altered optical train is implemented by adding a demagnification lens to optimize resolution for cytometry and to increase imaging speed.

Moreover, the addition of the demagnification lens (e.g., a 0.8× or less, 0.7× or less (e.g., 0.63×), 0.6× or less, 0.5× or less, or within a range from 0.4× to 0.8×, or from 0.5× to 0.7×), to the optical train achieves the minimum resolution needed for robust cytometry analysis. Demagnification enables imaging more surface area/image leading to 3-fold improvement in imaging speed while maintaining the high NA of the 10× objective.

Software development enables use of a higher powered light source, which facilitated lower exposure times for same sensitivity. A CMOS camera replaces an EMCCD to increase number of pixels by 16-fold, which enabled imaging at a 1.6-fold larger field of view and reduced imaging time by half.

Hardware triggering of all components, for example, controlled by TTL triggering using a commercial microcontroller (Arduino) with local memory, is implemented to achieve imaging speeds currently not provided by standard systems. As a result, the computer does not need to communicate with any hardware during an imaging run, which reduces imaging time by 40%.

Figure 12:
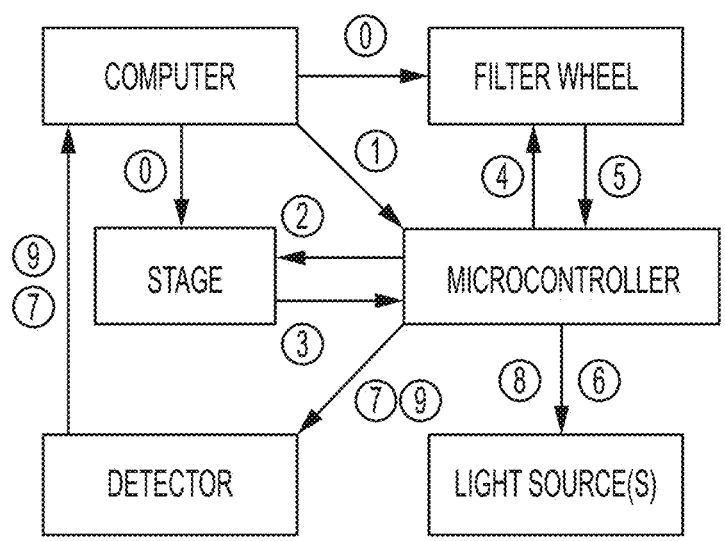
FIG. 12 shows hardware triggering of an exemplary imaging system.

To enable efficient communication between various components of the imaging system, the components are connected to a microcontroller capable of sending and receiving digital (e.g., TTL) signals with minimum (e.g., on the order of μs) delays and without interaction with a computer (FIG. 12). This approach leads to a considerable speed-up of acquisition of multi-spectral data across multiple spatial positions, since the delays normally introduced by slow serial connections, as well as systems-level inefficiencies of the software running on the computer, are factored out.

Acquisition time is defined only by movements of mechanical parts of the imaging system, triggering of the light source(s), as well as intervals of exposure of the detector to light and/or readout of signal from the latter. An efficient triggering scheme comprises the following steps, as depicted in FIG. 12:

0. Computer transmits spatial positions to the memory of Stage, and filter positions to the memory of Filter Wheel (additionally, Computer pre-arranges filter positions to minimize Filter Wheel movements). Other fixed parameters (e.g., EM gain for Detector) can also be pre-populated as appropriate. This transfer can be done over a slow (e.g., serial) link.
1. Computer transmits other parameters of acquisition (e.g., the number of positions and spectral channels to be acquired, as well as Light Source(s), exposure times and Filter Wheel movements to be set for each channel) to Microcontroller. This transfer can also be done over a slow (e.g., serial) link. This step is not typical for imaging microscopes. The information is transmitted to the system for processing all at once rather than typical serial handshaking serial processing with the computer and hardware. It allows the microcontroller to perform the acquisition without constantly checking with the computer.
2. Microcontroller starts a cycle of acquisition by signaling Stage to move to the next position stored in its memory in step 0.
3. Stage moves to the stored position and signals Microcontroller upon completion of the move.
4. Microcontroller signals Filter Wheel to move to the next position stored in its memory in step 0.
5. Filter Wheel moves to the stored position and signals Microcontroller upon completion of the move. To save time, steps 4 and 5 for the first Filter Wheel position may be performed between steps 2 and 3, since Stage movements typically take longer than Filter Wheel movements (e.g., 150 ms vs 50 ms).
6. Microcontroller signals Light Source(s) to turn them on. The time spent on ramping up light intensity to a full level is typically negligible (e.g., 10 μs<<1 ms) for solid state sources, in which case no signal needs to get sent back from Light Source(s), but rather a small delay (e.g., 1 ms) can be introduced to allow for this step to complete.
7. Microcontroller signals Detector to start integration of light.

8. Upon completion of exposure time, Microcontroller signals Light Source(s) to turn them off.
9. Microcontroller signals Detector to stop its integration. Detector automatically transfers accumulated image to a frame grabber on the computer. Depending on the model of Detector, this transfer can be done simultaneously with step 7.
10. Steps 4-9 are repeated for the rest of spectral channels in the current spatial position.
11. The next cycle of acquisition begins, starting with step 2.

A micromanipulator is integrated into imaging hardware and software so that it is not necessary to transfer cells to another machine and recalibrate.

Real-time processing of image data is implemented. By contrast, processing of data via other methods can take a couple hours, which dramatically slows time for picking cells.

Moreover, the imaging beam can be reconfigured to enable imaging of all channels utilizing the same excitation band simultaneously (e.g., in contrast to serially (e.g., typically 4-6 channels per excitation)). This process is often called imaging spectrometry, which includes a series of dichroic mirrors to split image into separate image beams based on different wavelengths and then all beams are aimed at different sections of the same CMOS camera, taking 5 or 6 non-overlapping images at the same time. This cuts the number of images required for 16 colors from 16 to 4, leading to a 3-fold increase in imaging speed.

In certain embodiments, a second light source is added to bring the number of available spectral channels to 23 channels, higher than any commercial flow cytometer. This feature emphasizes that the scaling of the machine for new channels is far more efficient than flow cytometry designs because the same detection channels are used for all excitation wavelengths. In contrast, flow machines must duplicate these processes because the cells are moving past the detectors.

Moreover, a square excitation field stop can be added, which, in certain embodiments, is critical for tissue imaging applications by limiting illumination to only square being imaged, thereby preventing photobleaching.

The following is an illustrative list of steps performed in a triggering experiment, together with their timings:
Position 0 started
Wheel moved. 55 msec
Stage moved. 106 msec
Channel 0 acquired. 207 msec
Wheel moved. 54 msec
Channel 1 acquired. 157 msec
Channel 2 acquired. 101 msec
Channel 3 acquired. 101 msec
Wheel moved. 54 msec
Channel 4 acquired. 256 msec
Channel 5 acquired. 201 msec
Wheel moved. 56 msec
Channel 6 acquired. 157 msec
Channel 7 acquired. 101 msec
Channel 8 acquired. 101 msec
Wheel moved. 100 msec
Channel 9 acquired. 201 msec
Wheel moved. 56 msec
Channel 10 acquired. 157 msec
Wheel moved. 54 msec
Channel 11 acquired. 156 msec
Position 0 acquired
Total time: 1896 msec Innovation in Imaging Optics to Enable Precise Image Spectrometry of Wide Field, High Aperture Images To enable precise imaging spectrometry of wide-field high aperture images, the imaging beam is separated as a converging beam instead of collimated beam. In contrast to a converging beam, a collimated beam of a wide field image becomes far too wide for efficient optical separation. A converging beam enables fast, high-throughput imaging and analysis.

Figure 14A:
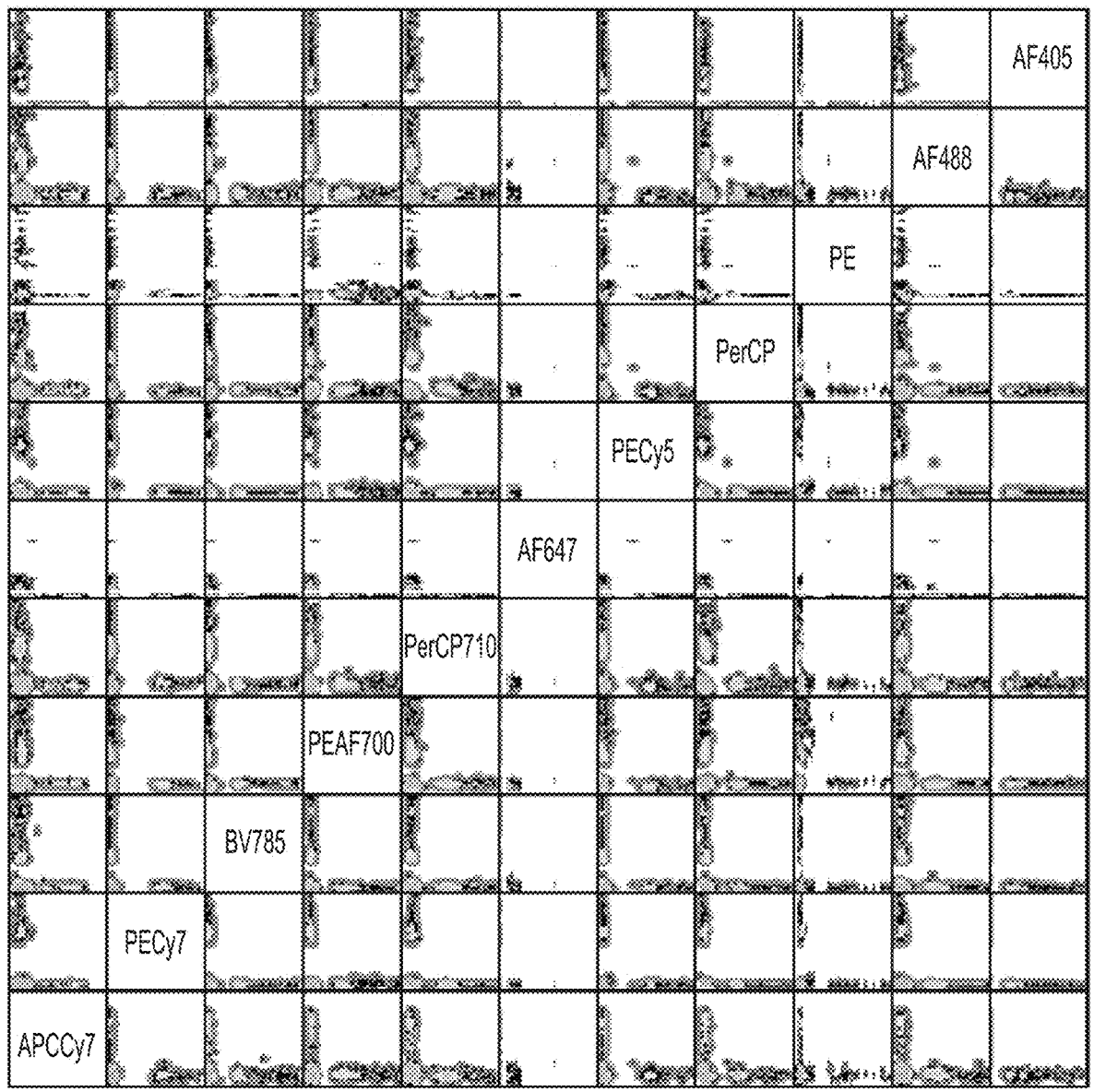
FIG. 14A shows a scatter plot of beads that were labeled individually with 11 different fluorophores and imaged using the triggering procedure described herein. The intensity of fluorescence after compensation for all beads is plotted. Each bead displays signal in only a single channel (all beads align along the axes of each plot).

FIG. 14A is a scatter plot depicting beads that were labeled individually with 11 different fluorophores and imaged. The intensity of fluorescence after compensation for all beads is plotted. Each bead displays signal in only a single channel (all beads align along the axes of each plot). Polystyrene beads coated with anti-mouse antibody were used to bind mouse antibodies labeled with BV785, AF488, PerCP, PerCP710, PE, PECy5, PEAF700, PECy7, AF647, and APCCy7. Calcein violet was used to stain human PBMC. Each individually stained bead or cell was loaded into a well of a 96 well plate and all wells were imaged in 11 spectral channels using the Present system. The intensity of each bead in all spectral channels was extracted. The average spillover signal from each fluorophore in each spectral channel was calculated. The spectral data was used to compensate the signal emitted by each bead. The compensated data for all the beads and cells was then pooled and 2D scatter plots comparing the compensated signal each channel compared to all other channels is displayed.

Figure 14B:
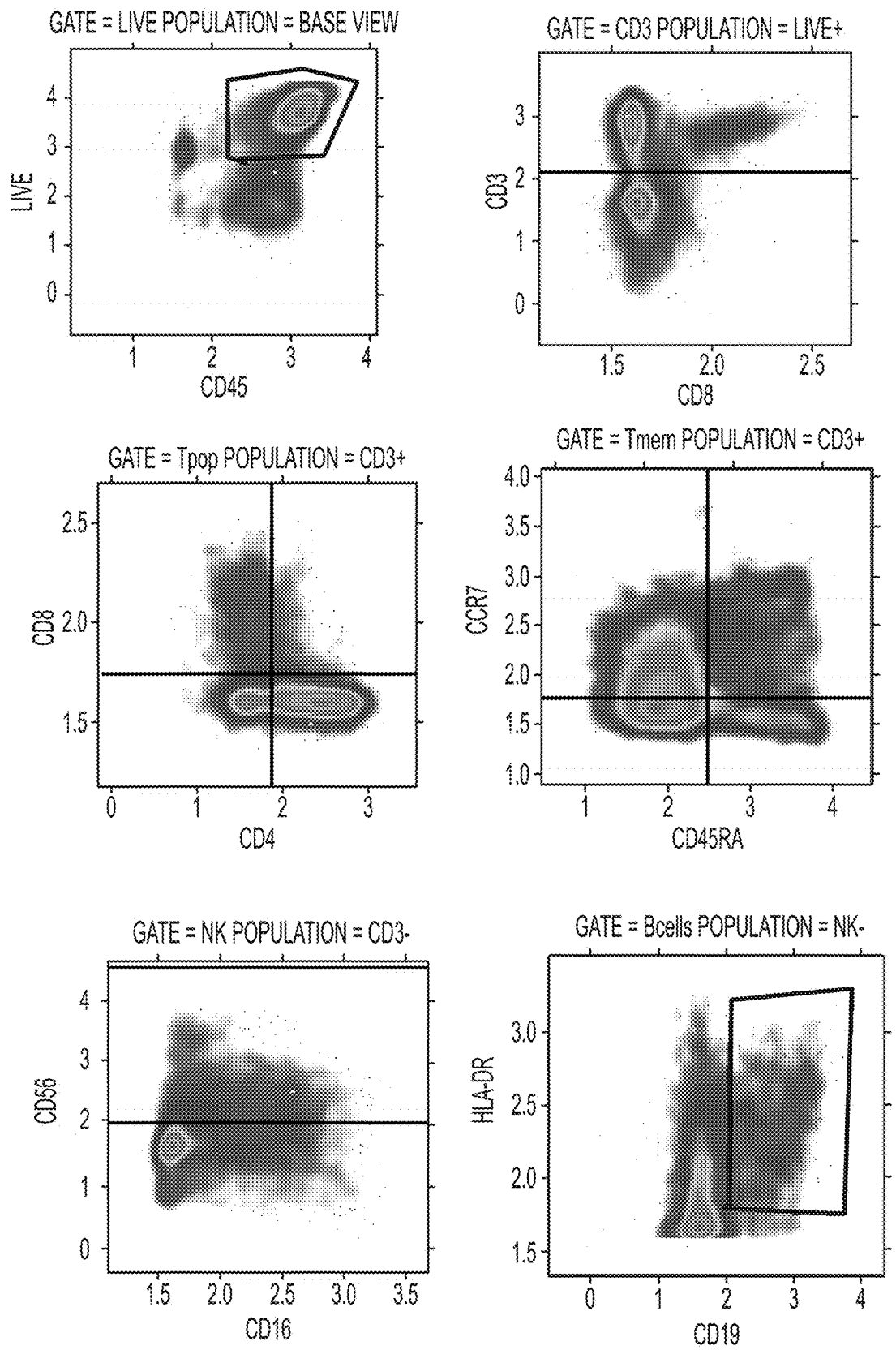
FIG. 14B shows cells that were labeled with fluorescent markers and imaged on the Present system using the triggering procedure, as described herein, at a speed of 60 mm$^2$/min for 12 channels. Hierarchical gating of the data after data extraction and compensation is displayed for some common cell phenotypes.

FIG. 14B shows cells that were labeled with fluorescent markers and imaged on the Present system at a speed of 60 mm2/min for 12 channels. Hierarchical gating of the data after data extraction and compensation is displayed for some common cell phenotypes.

Human peripheral blood mononuclear cells were labeled with BV785-HLADR, AF488-CCR7, PerCP-CD3, PerCP710-CD16, PE-CD19, PECy5-CD56, PEAF700-CD4, PECy7-CD45RA, AF647-CD45, and APCCy7-CD8 antibodies. The cells were loaded into an array of 50 um$^3$ wells molded in PDMS on a glass slide. The array was imaged using the Present system at a speed of 60 mm$^2$/min for 12 channels (11 fluorescent+transmitted light). The intensity of signal in each spectral channel was extracted from each image. The data was compensated using spectral spillover values measured using singly stained beads. The resulting data was logicle transformed and hierarchically gated using 2D scatter plots to identify common cell phenotypes.

Data was acquired on a microscope of the Present system consisting of a frame (ASI), filter wheel (ASI), TI2500 stage (ASI), 125D tube lens (ASI), TI2500 automated stage (ASI), ImageEM EMCCD camera (Hamamatsu), dichroic cube, SpectraX light engine (Lumencor), a LED light for transmitted light and a 10×/0.3NA Plan apochromatic objective (Olympus). All filters and the dichroic mirror were acquired from Semrock except the 710/20 and 810/80 filters (Omega). Each channel was acquired for 100 msec at a gain of 10 and excitation power of 100%. The stage, filter wheel, light source and camera were all controlled through TTL triggering using an Arduino board. The filters were used in the following combinations to create the indicated spectral channel:

| Spectral channel | Exc. | Em. |
| --- | --- | --- |
| Calcein Violet | 380/14 | 440/40 |
| BV785 | 380/14 | 810/80 |

| Spectral channel | Exc. | Em. |
|---|---|---|
| AF488 | 485/25 | 525/39 |
| PerCP | 485/25 | 684/24 |
| PerCP710 | 485/25 | 710/20 |
| PE | 560/25 | 607/36 |
| PECy5 | 560/25 | 684/24 |
| PEAF700 | 560/25 | 710/20 |
| PECy7 | 560/25 | 810/80 |
| AF647 | 648/20 | 684/24 |
| APCCy7 | 648/20 | 810/80 |

Figure 15:
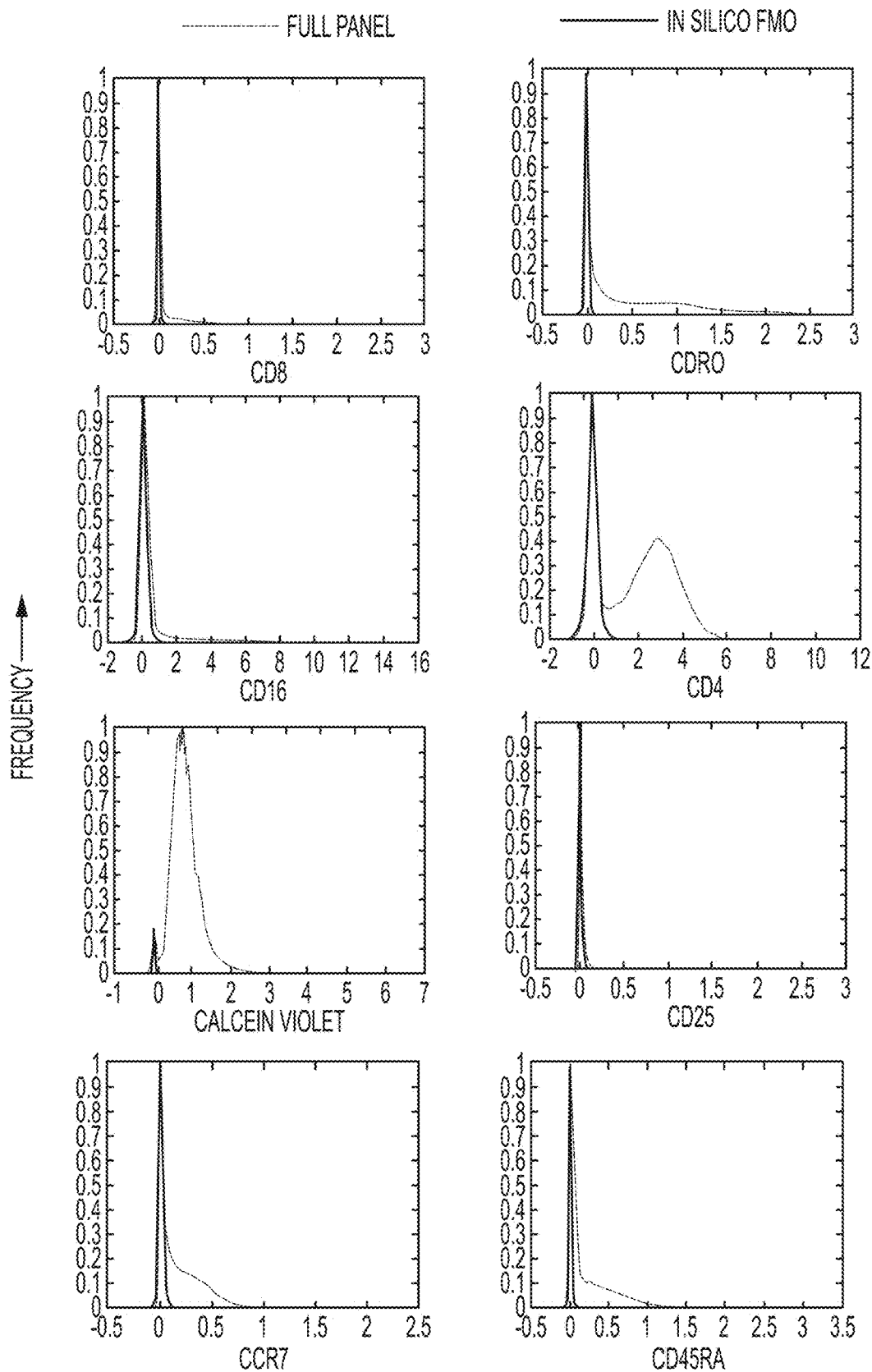
FIG. 15 shows plots of fluorescent intensities of cells extracted from a set of images by nanobox and in silico FMO.

FIG. 15 shows plots of fluorescent intensities of cells extracted from a set of images by nanobox and in silico FMO. Human PBMC were stained with CD4-PEAF700, CD16-PerCP710, CD3-PerCP, CD45RO-PECy5, CD8-APCCy7, CD45RA-PECy7, CCR7-PE, CD25-BB515 antibodies and calcein violet live stain. Cells were loaded into a nanowell array and imaged in 9 spectral channels. Fluorescent intensities of each cell were extracted from the images by nanobox and in silico FMO were generated from the data. The in silico FMO were generated for each channel except CD3, which was used to identify cell locations (and could not be used for FMO generation), and are plotted with their corresponding plots of the fully stained cells.

EQUIVALENTS

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A system for automated identification and recovery of individual cells of interest, the system comprising:
    a microscope comprising a light source, an optical train, and a detector capable of imaging a deposition-well plate positioned on a motorized stage;
    a motorized stage and a set of actuators configured to translate the stage in a first direction and a second direction in a horizontal plane;
    a motorized focus drive to translate an optical objective of the microscope in a vertical direction;
    a micromanipulator arm comprising an actuator configured for constrained movement of the micromanipulator arm in the vertical direction to calibrate a location of a capillary needle within an imaging field of view of the detector, wherein the capillary needle is removably fastened/fastenable to the micromanipulator arm and oriented in the vertical direction;
    one or more deposition-well plates comprising one or more sample wells and/or one or more recovery wells, wherein the deposition-well plates are removably attached/attachable to the motorized stage; and
    a processor of a computing device, wherein the processor is configured to send a series of control signals to cause:
        (i) the microscope to capture an image of a first sample well, wherein the processor is further configured to analyze the image to identify a location of an individual cell of interest within the first sample well;
        (ii) the set of actuators to translate the motorized stage according to the identified location of the individual cell of interest within the first sample well, such that the capillary needle is oriented above the individual cell of interest;
        (iii) the actuator to translate, in the vertical direction, the micromanipulator arm to orient a tip of the capillary needle in the first sample well at or sufficiently near the individual cell of interest;
        (iv) introduction of a volume of fluid comprising the individual cell of interest into the capillary needle;
        (v) the actuator to translate, in the vertical direction, the micromanipulator arm such that the capillary needle containing the volume of fluid comprising the individual cell of interest is raised out of the first sample well;
        (vi) the set of actuators to translate the motorized stage, such that the capillary needle containing the volume of fluid comprising the individual cell of interest is oriented above the first recovery well;
        (vii) the actuator to translate, in the vertical direction, the micromanipulator arm such that the capillary needle containing the volume of fluid comprising the individual cell of interest is lowered into the first recovery well; and
        (viii) a release of the volume of fluid thereby depositing the individual cell of interest into the first recovery well; and
    wherein the processor is configured to perform a multi-point calibration of a surface of the deposition-well plate to correct spatial variations in three-dimensional space, thereby providing a coordinate system enabling the microscope stage and the motorized focus drive to be automatically translated by the processor,
    wherein the multi-point calibration comprises
        positioning the motorized stage at positions corresponding to one or more locations of an imaging region of the deposition-well plate;
        identifying coordinates corresponding to these locations; and
        using the coordinates to extrapolate one or more points corresponding to one or more additional positions within the imaging region, respectively, thereby correcting for spatial variations of the deposition-well plate.

2. The system of claim 1, wherein the capillary needle is or comprises steel, glass, or plastic.

3. The system of claim 1, the system further comprising:
    a back-light illumination system co-located with the micromanipulator arm and capillary needle and oriented to project light such that the microscope collects sufficient transmitted light to image and analyze the individual cell of interest in this channel.

4. The system of claim 1, wherein the processor is configured to perform an automated search for specific points on the deposition-well plate using a software image analysis algorithm to detect the specific points.

5. The system of claim 1, wherein the processor is configured to perform multi-point calibration of imaging focus at one or more select locations of the deposition-well plate using a software autofocus algorithm comprising a focus scoring method and a one-dimensional root-finding algorithm, and extrapolating the multi-point calibration for a plurality of other locations of the deposition-well plate.

6. The system of claim 1, wherein the processor is configured to determine a spatial position of the tip of the capillary needle based on one or more needle calibration images.

7. The system of claim 1, wherein the introduction of the volume of fluid comprising the individual cell of interest into the capillary needle and the release of the individual cell of interest into the first recovery well are conducted with or without a working fluid, and/or with or without a micropump.

8. The system of claim 7, wherein the introduction of the volume of fluid comprising the individual cell of interest into the capillary needle and the release of the individual cell of interest into the first recovery well are further controlled by the processor based on an image analysis algorithm and spatial data structure designed to trace locations of individual cells on the first recovery well and/or the capillary needle.

9. The system of claim 1, wherein the individual cell of interest is a member selected from the group consisting of a circulating tumor cell (CTC), a lymphocyte, a leukocyte, a tumor cell, a stromal cell, a neuronal cell, a cell line, a stem cell, and an embryo.

10. The system of claim 1, the system comprises a module ("Nanobox") to automatically identify candidate individual cells of interest, present images of candidate cells to a user, and automatically transfer chosen cells into recovery wells.

11. The system of claim 10, wherein the system is further configured to detect and present dynamic behaviors of individual cells of interest based on images taken at multiple time points;

to trace the locations of individual cells of interest over time; and to resolve potential duplicates amongst candidate cells of interest due to an overlap between adjacent images.

12. The system of claim 10, wherein the processor is further configured with a module to define an optimal set of fluorescence intensity thresholds based on statistical and/or visual analysis performed simultaneously with loading and processing of images; and/or to simultaneously present the images under screen cursor in all channels and mark by a user locations of true positive individual cells of interest that are either detected correctly or missed by the processor.

13. The system of claim 1, wherein the cell of interest is a Chinese Hamster Ovary (CHO) cell.

14. The system of claim 10, wherein the module identifies individual cells of interest based on cell morphology.

15. The system of claim 10, wherein the module presents images of candidate cells to a user assisted by a machine learning algorithm.

16. The system of claim 15, wherein the machine learning algorithm is configured to suggest individual cells of interest.

* * * * *

UNITED STATES PATENT AND TRADEMARK OFFICE
CERTIFICATE OF CORRECTION

PATENT NO. : 10,776,608 B2
APPLICATION NO. : 16/102118
DATED : September 15, 2020
INVENTOR(S) : Viktor Adalsteinsson et al.

Page 1 of 1

It is certified that error appears in the above-identified patent and that said Letters Patent is hereby corrected as shown below:

In the Claims

In Claim 10, Column 39, Line 19, please insert --wherein-- between "claim 1," and "the system comprises a module".

Signed and Sealed this
Seventeenth Day of November, 2020

Andrei Iancu
*Director of the United States Patent and Trademark Office*